(12) United States Patent
Stoddard et al.

(10) Patent No.: US 11,241,591 B2
(45) Date of Patent: Feb. 8, 2022

(54) ACOUSTIC MODULE AND CONTROL SYSTEM FOR HANDHELD ULTRASOUND DEVICE

(71) Applicant: Access Business Group International LLC, Ada, MI (US)

(72) Inventors: Ronald L. Stoddard, Kentwood, MI (US); Michael E. Miles, Grand Rapids, MI (US); Matthew J. Norconk, Grand Rapids, MI (US); Joshua K. Schwannecke, Grand Rapids, MI (US); Joseph C. Van Den Brink, Coopersville, MI (US); Colin J. Moore, Grand Rapids, MI (US); A. Esai Umenei, Grand Rapids, MI (US); Ryan D. Schamper, Grand Haven, MI (US); Mark S. Bartrum, Avon, OH (US); Benjamin C. Moes, Wyoming, MI (US); Karlis Vecziedins, Caledonia, MI (US); Ziqi Wu, Grand Rapids, MI (US); Mark C. Smith, Rockford, MI (US); Bradley J. Pippel, Grandville, MI (US); David S. Vachon, Fennville, MI (US)

(73) Assignee: Access Business Group International LLC, Ada, MI (US)

( * ) Notice: Subject to any disclaimer, the term of this patent is extended or adjusted under 35 U.S.C. 154(b) by 848 days.

(21) Appl. No.: 15/234,217

(22) Filed: Aug. 11, 2016

(65) Prior Publication Data
US 2017/0043189 A1 Feb. 16, 2017

Related U.S. Application Data

(60) Provisional application No. 62/204,656, filed on Aug. 13, 2015, provisional application No. 62/339,195, filed on May 20, 2016.

(51) Int. Cl.
*A61N 7/00* (2006.01)
*G10K 11/24* (2006.01)
(Continued)

(52) U.S. Cl.
CPC .............. *A61N 7/00* (2013.01); *A61B 8/4281* (2013.01); *A61N 7/02* (2013.01); *G10K 11/24* (2013.01);
(Continued)

(58) Field of Classification Search
None
See application file for complete search history.

(56) References Cited

U.S. PATENT DOCUMENTS 5,402,793 A * 4/1995 Gruner ................ A61B 1/0052
600/447
5,560,362 A * 10/1996 Sliwa, Jr. .............. A61B 8/546
600/439
(Continued)

FOREIGN PATENT DOCUMENTS

| CN | 101336121 | 12/2008 |
|---|---|---|
| CN | 102573983 | 7/2012 |
| WO | 2011/020097 | 2/2011 |

OTHER PUBLICATIONS

Garcia, Mónica Delgado. "Analysis of microencapsulated phase change material slurries and phase change material emulsions as heat transfer fluid". Doctorate from Universidad De Zaragoza. 2013. pp. 1-319. (Year: 2013).*
(Continued)

*Primary Examiner* — James M Kish
(74) *Attorney, Agent, or Firm* — Warner Norcross + Judd LLP

(57) ABSTRACT

An acoustic module with a transducer and a solid waveguide. The transducer and waveguide may be curved to
(Continued)

focus the acoustic energy along a focal line. The transducer, the top surface of the waveguide and the bottom surface of the waveguide may extend along coaxial curves. The waveguide may include a recess closely receiving the transducer. The waveguide may include an integral skirt that provides a thermal mass. The acoustic module may include a space to accommodate thermal management options. For example, the acoustic module may include a heatsink, an active ventilation system and/or a phase change material. The ultrasound device may include a controller configured to perform a uniformity scan sweep during supply of operating power to the transducer. The uniformity scan sweep can extend through a frequency range that includes the operating point of the acoustic module and does not exceed an acceptable efficiency loss.

46 Claims, 20 Drawing Sheets

(51) Int. Cl.
*A61B 8/00* (2006.01)
*A61N 7/02* (2006.01)

(52) U.S. Cl.
CPC  *A61N 2007/006* (2013.01); *A61N 2007/0034* (2013.01); *A61N 2007/0086* (2013.01)

(56) References Cited

U.S. PATENT DOCUMENTS

| | | | |
|---|---|---|---|
| 5,735,280 A * | 4/1998 | Sherman | A61B 17/2202 600/1 |
| 6,666,835 B2 | 12/2003 | Martin et al. | |
| 9,694,211 B2 | 7/2017 | Barthe et al. | |
| 9,694,212 B2 | 7/2017 | Barthe et al. | |
| 2001/0021807 A1* | 9/2001 | Saito | B06B 1/067 600/437 |
| 2004/0049134 A1 | 3/2004 | Tosaya et al. | |
| 2005/0075573 A1* | 4/2005 | Park | A61B 8/00 600/459 |
| 2006/0184071 A1 | 8/2006 | Klopotek | |
| 2006/0191344 A1* | 8/2006 | Hashimoto | A61B 8/00 73/632 |
| 2008/0027328 A1* | 1/2008 | Klopotek | A61B 8/4281 600/472 |
| 2008/0195003 A1* | 8/2008 | Sliwa | A61N 7/02 601/3 |
| 2009/0062697 A1 | 3/2009 | Zhang et al. | |
| 2009/0112098 A1* | 4/2009 | Vaezy | A61B 8/546 600/459 |
| 2009/0275832 A1* | 11/2009 | Gelbart | A61B 8/08 600/439 |
| 2010/0198064 A1* | 8/2010 | Perl | A61H 23/0245 600/439 |
| 2011/0270137 A1 | 11/2011 | Goren et al. | |
| 2012/0143060 A1* | 6/2012 | Weekamp | A61B 8/546 600/459 |
| 2013/0197550 A1 | 8/2013 | Dietz et al. | |
| 2015/0161982 A1 | 6/2015 | Laugharn et al. | |

OTHER PUBLICATIONS

International Search Report and Written Opinion of International Application No. PCT/US2016/046454, dated Jan. 30, 2017.

* cited by examiner

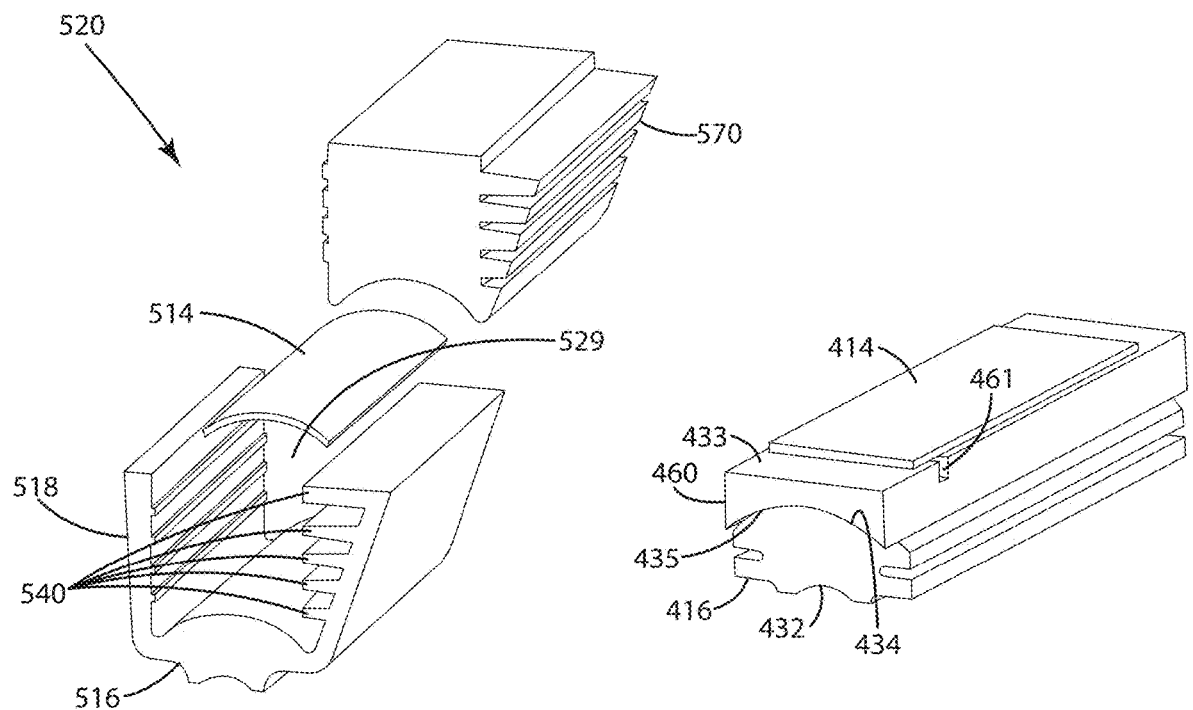
Fig. 15
Fig. 17
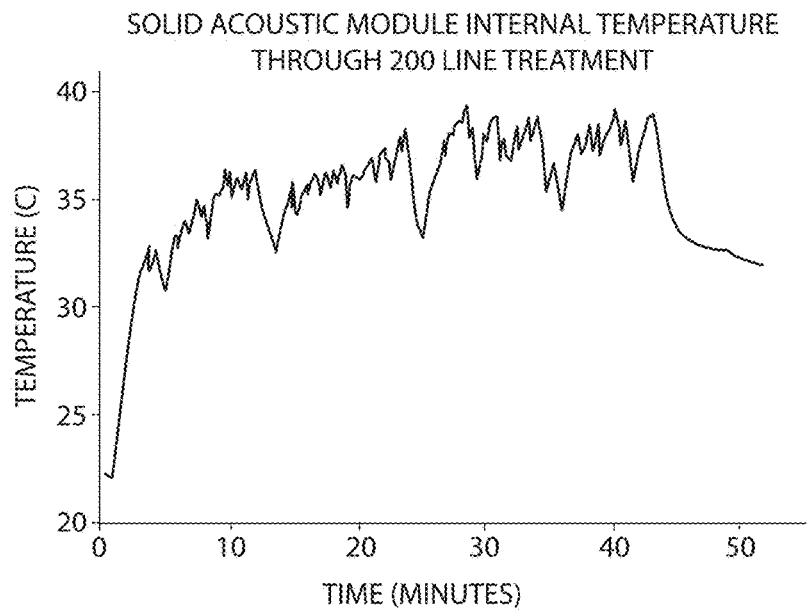
Fig. 16

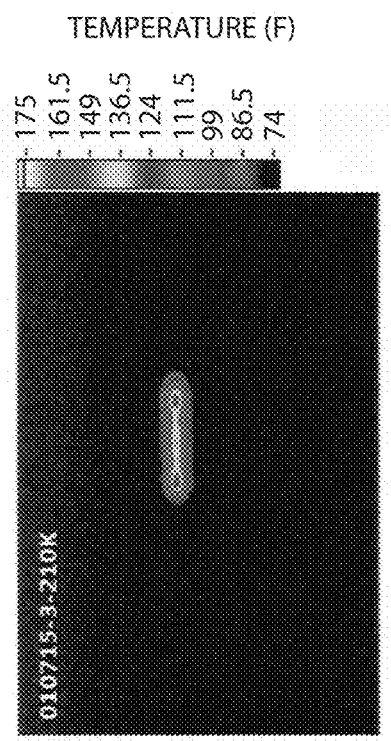
Fig. 20A
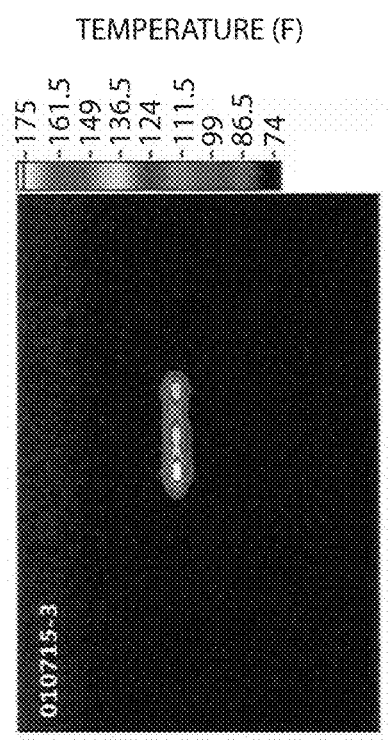
Fig. 21A
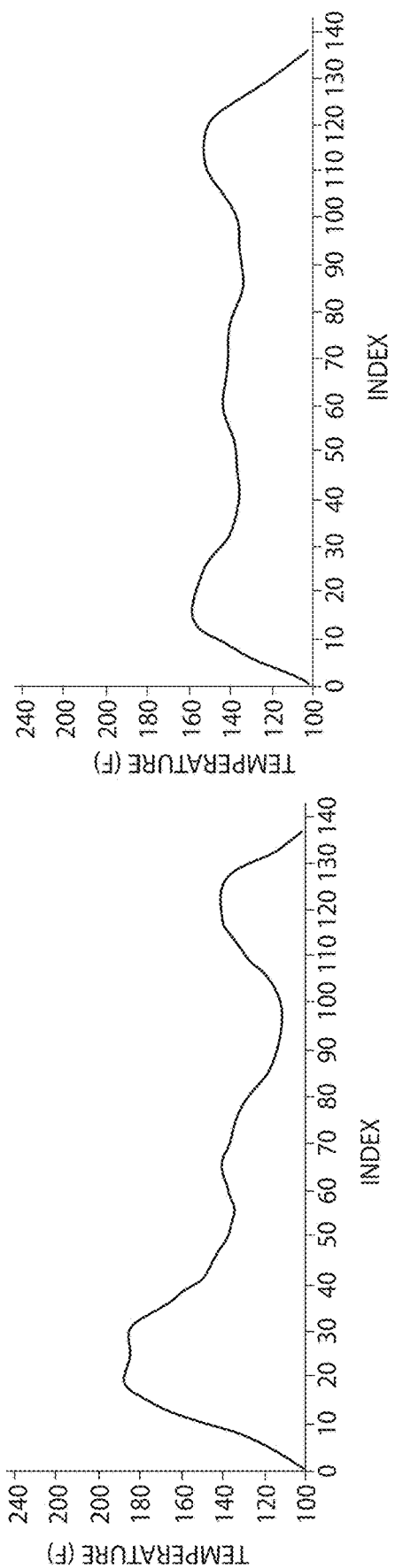
Fig. 20B
Fig. 21B

ACOUSTIC MODULE AND CONTROL SYSTEM FOR HANDHELD ULTRASOUND DEVICE

BACKGROUND OF THE INVENTION

The present invention relates to ultrasound devices, and more particularly to an acoustic module and a control system for operating an ultrasound device incorporating an acoustic waveguide.

Ultrasound devices have been developed for use in a variety of therapeutic applications. These devices produce ultrasound or acoustic energy that can be applied to the human body for therapeutic purposes. For example, there are a variety of conventional ultrasound devices used to apply acoustic energy to the skin to promote the generation of new collagen that has the effect of reducing fine lines, wrinkles and sagging skin.

Typical handheld ultrasound devices include a transducer to generate the ultrasound energy and a lens to provide proper focus to the ultrasound energy. Often, the transducer and lens are situated in an acoustic module that houses the transducer and lens and includes a contact membrane (or other surface) configured to directly engage the target. The intervening space between the lens and the contact membrane is typically filled with a liquid, such as water, that functions as a medium for the ultrasound energy to travel from the lens to the contact membrane. Bubbles and other imperfections within the water (or other liquid medium) can affect the acoustic field and negatively impact operation of the device. This has proven to be a significant drawback because experience has revealed that it is difficult to keep bubbles from forming within water and other liquid mediums between the lens and the contact membrane. Another significant drawback is that water has the potential to freeze, for example, during warehouse storage, transportation and other stages of distribution. Freezing water expands, which can rupture the water vessel and allow thawed water to leak out and render the product non-functional.

Other manufacturing issues present additional practical issues that can negatively impact device performance—perhaps most notably by impairing consistency and reducing uniformity of acoustic fields generated by the device. For example, it can be difficult to secure the transducer to the lens without imperfections. Imperfections in the interface between the transducer and the lens can have a negative impact on performance in various ways, for example, by reducing uniformity in acoustic output or by reducing efficiency. To illustrate, in some devices, the transducer is secured to the lens by epoxy or other adhesives. In many applications, gaps or variations in the thickness of the epoxy can have a substantial negative impact on performance. Further, even seemingly small differences in the location at which the transducer is affixed to the lens can impair performance. As a result of these and other practical difficulties, it can be difficult to produce a handheld ultrasound device that operates at optimal efficiency or provides uniform acoustic output across its head. It can also be difficult to maintain consistency in the acoustic fields generated by each separately manufactured ultrasound device.

A number of additional complications can be presented by the membrane used to contain the liquid. As one example, it can be difficult and costly to provide a membrane that satisfies the desired tolerance requirements. As another example, the membrane can have a negative effect on the ability of the system to detect when it is properly coupled with the target. Further, the membrane can effect in temperature rise and its thickness can affect efficiency and power draw.

The design of ultrasound devices is further complicated by the fact that conventional ultrasonic transducers generate a significant amount of thermal energy. Too much heat can have a negative impact on the electronic components of the device. It can also make it uncomfortable to place the device against human skin.

SUMMARY OF THE INVENTION

The present invention provides a solid waveguide for use with a handheld ultrasonic device. The transducer is joined to the solid waveguide so that acoustic energy produced by the transducer is communicated directly into the waveguide. In one embodiment, the interface between the transducer and the waveguide is curved. In one embodiment, the waveguide has an exposed contact surface intended to be placed in contact with the target. The contact surface may be curved to help in focusing the acoustic energy and to provide a surface particularly well-suited to receive an ultrasound gel. The transducer interface surface and the contact surface may be concentric. The transducer may be a piezo ceramic transducer that vibrates in response to the application of electrical power. The solid waveguide may be manufactured from a single piece of aluminum.

In one embodiment, the solid waveguide may include an epoxy or adhesive ridge that surrounds the transducer. The ridge may be formed by epoxy or adhesive that has been forced out from between the transducer and the waveguide when transducer is affixed to the waveguide. The waveguide may include a small rib configured to forming the oozing epoxy or adhesive into the desired ridge.

In one embodiment, the solid waveguide includes a transducer surface having a pocket that is configured to receive the transducer. The pocket may be defined as a shallow recess in the surface of the solid waveguide. The recess may be curved to facilitate mounting of the transducer in the desired curved shape.

In one embodiment, the ultrasound head incorporating the solid waveguide includes a thermal absorbing material that undergoes a phase change in response to the heat energy created during normal use of the ultrasound device. The thermal absorbing material may be disposed in a cavity disposed behind the transducer and solid waveguide. The thermal absorbing material may be any of a wide variety of phase change materials ("PCM"), such as paraffin, PCM wax, microencapsulated PCMs or other high heat capacity materials. The use of thermal absorbing materials, such as PCMs, is optional and the present invention may be implemented without PCMs or other thermal absorbing materials.

In one embodiment, the solid waveguide includes an integral skirt that extends rearwardly to form an enclosure that defines a cavity behind the transducer. With this embodiment, the solid waveguide may form the head of the acoustic module or the solid waveguide may be contained within a separate outer housing. The cavity may include a heat sink and/or contain a thermal absorbing material, such as a PCM. Alternatively, the cavity may be empty, which would still allow some level of heat transfer through air convection.

In one embodiment, the solid waveguide is disposed within a separate acoustic enclosure. In such embodiments, the solid waveguide may include wings that extend rearwardly to provide improved heat transfer. The wings may include a plurality of fins that increase surface area and improve thermal transfer. The wings may be formed integrally with the solid waveguide or they may be separately manufactured and later joined to (or placed in contact with) the solid waveguide.

In one embodiment, the solid waveguide is incorporated into an actively vented acoustic module. In this embodiment, a micro-fan may be disposed within the cavity in the acoustic module to move air through the enclosure to provide improved cooling. The fan may be configured to move air into the acoustic module through an inlet and out of the acoustic module through an outlet. The inlet and outlet may be covered by air permeable membranes that allow air, but not water or debris to pass. If the acoustic module includes a heat sink, the fan, inlet and outlet may be arranged so that air is moved over the fins or other features of the heat sink.

In another embodiment, the acoustic module includes a transducer, a lens and a solid waveguide. In this embodiment, the lens may be situated between the transducer and the solid waveguide. The lens may help to focus the ultrasound energy before transmitting it to the waveguide. In one embodiment, the lens is manufactured from aluminum and the solid waveguide is manufactured from a plastic with appropriate acoustic properties, such as Rexolite® plastic.

In one embodiment, the present invention provides a control method for improving uniformity in the acoustic output of an acoustic module. Generally, the method involves implementing a frequency sweep during the application of operating power to the transducer. The frequency sweep may extend across a predefined uniformity scan window. The uniformity scan window may include the operating point of the acoustic module. By sweeping through a range of frequencies while applying operating power, the system can dramatically improve overall acoustic uniformity. In one embodiment, the uniformity sweep can occur continuously and repeatedly while the controller is providing operating power to the transducer. In other embodiments, the uniformity sweep can be discontinuous.

In one embodiment, the uniformity scan window is centered on the operating point of the acoustic module. In one embodiment, the uniformity scan window may have a step size and step time. The step size and step time may be predetermined or may be determined on an acoustic module-by-acoustic module basis. For example, the step size and or step time may be determined based on the uniformity scan window. The step size and/or step time may be selected to provide a generally linear sweep or to provide a non-linear sweep, such as a random sweep.

In one embodiment, the method is implemented by separately determining the uniformity scan window for each acoustic module following production of that acoustic module. The method of determining the uniformity scan window may include the steps of (a) applying power to the acoustic module at a variety of different frequencies, (b) determining the efficiency of the acoustic module at the various applied frequencies and (c) selecting the uniformity scan window to be a window that is as large as possible without exceeding a predetermined efficiency loss. In one embodiment, the step of determining the efficiency of the acoustic module at various applied frequencies may include the step of comparing the efficiency of the acoustic module at its operating point with the efficiency of the acoustic module at the various applied frequencies. In one embodiment, the comparison step may include determining the percent efficiency loss at each of the various applied frequencies as compared to the operating point. The predetermined efficiency loss may vary from application to application, but in one embodiment may be about 5%.

The present invention provides a simple and effective solid waveguide. The solid waveguide helps to overcome limitations presented by devices that incorporate a fluid filled acoustic module. The solid waveguide will not produce bubbles or other imperfections in response to temperature and pressure changes. Further, certain materials that can be used to form the solid waveguide, such as aluminum, exhibit significantly less variation in acoustic properties in response to temperature variation than is generally found with conventional liquid medium. The solid waveguide can include curved surfaces that control the focus of the acoustic energy. Coaxial curved surfaces can provide efficient and effective transmission of acoustic energy from the transducer, through the waveguide to desired focal line. The waveguide may include slots that reduce fringe interference, while also providing a mounting slot for heat sink components, when desired. The acoustic module may include an enlarged space reward of the transducer/waveguide assembly to address thermal management issues. For example, a heat sink, an active ventilation system and/or phase change materials can be incorporated into the acoustic module in this space. Further, the system may provide improved uniformity of acoustic transmission by incorporating a uniformity scan algorithm that compensates for variations in the transducer and waveguide by performing a frequency sweep while applying operating power.

These and other objects, advantages, and features of the invention will be more fully understood and appreciated by reference to the description of the current embodiment and the drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components. Any reference to claim elements as "at least one of X, Y and Z" is meant to include any one of X, Y or Z individually, and any combination of X, Y and Z, for example, X, Y, Z; X, Y; X, Z; and Y, Z.

BRIEF DESCRIPTION OF THE DRAWINGS

FIG. 15 is an exploded perspective view of an acoustic module having an alternative waveguide and incorporating a phase change material.

FIG. 16 is a graph showing internal temperature of the acoustic module when incorporating the phase change material of FIG. 15.

FIG. 17 is a perspective view of an alternative composite waveguide.

FIG. 20A is a thermal image of acoustic module output without a uniformity scan algorithm.

FIG. 20B is a line graph of temperature over the width of the waveguide without a uniformity scan algorithm.

FIG. 21A is a thermal image of acoustic module output with a uniformity scan algorithm.

FIG. 21B is a line graph of temperature over the width of the waveguide with a uniformity scan algorithm.

DESCRIPTION OF THE CURRENT EMBODIMENT

Overview

Figure 1:
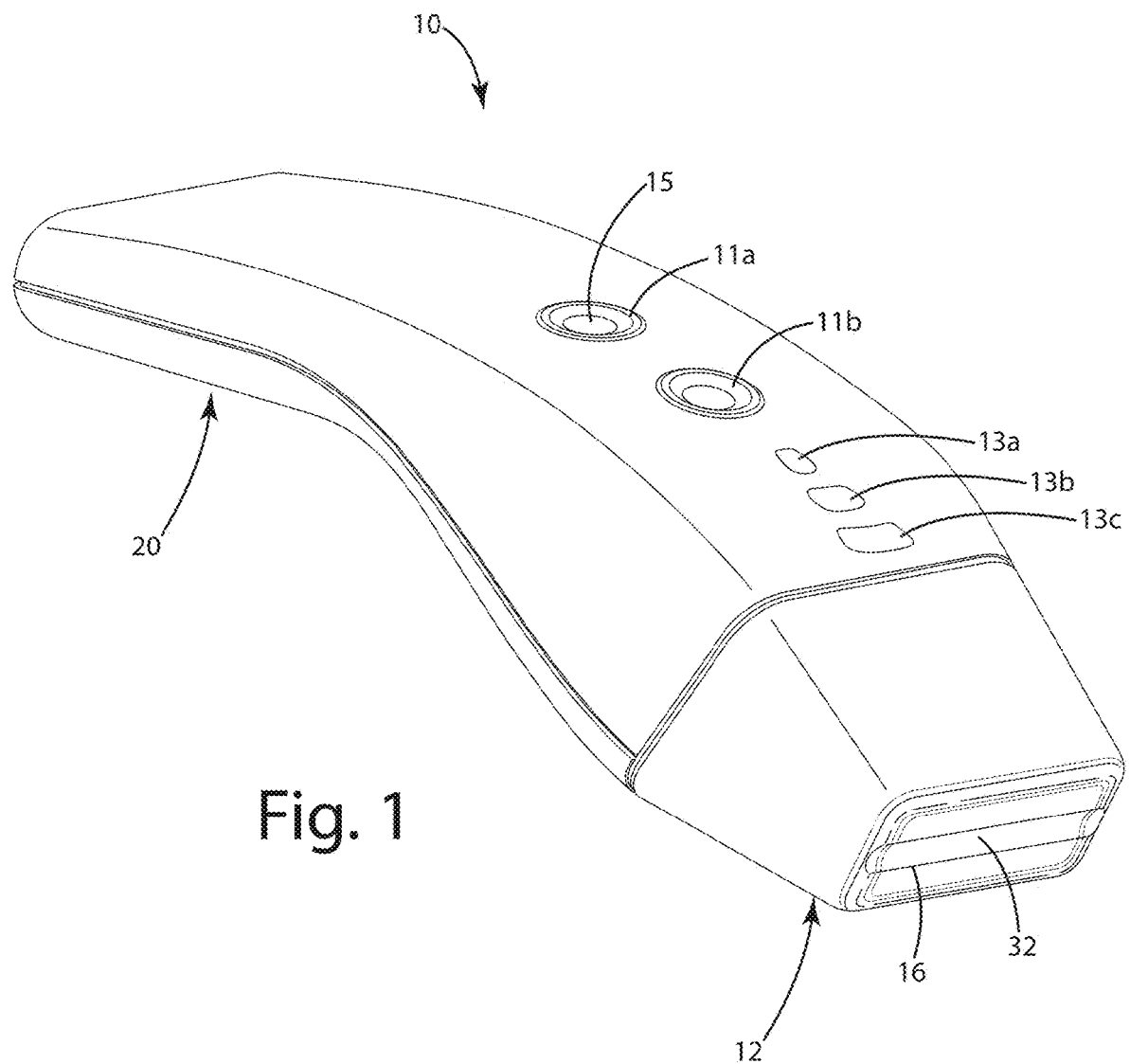
FIG. 1 is a perspective view of an ultrasound device incorporating a waveguide in accordance with an embodiment of the present invention.

An ultrasound device incorporating a solid waveguide in accordance with an embodiment of the present invention is shown in FIG. 1. The ultrasound device 10 includes an acoustic module 12 having a transducer 14 and a solid waveguide 16. In this embodiment, the transducer 14 is secured to the top surface of the waveguide 16, for example, by epoxy or other suitable adhesives. The ultrasound device 10 of this embodiment is configured to apply ultrasound energy to the user's skin and to focus the ultrasound energy at a depth of about 2 to 6 mm below the surface of the skin. To achieve the desired focus, the transducer 14 and waveguide 16 are curved. In the illustrated embodiment, the transducer 14, the top surface of the waveguide 16 and the bottom surface of the waveguide 16 extend along coaxial curves. If desired, the waveguide 16 may include a recess configured to closely receive the transducer 14.

The acoustic module 12 may include a space disposed behind the transducer 14 and waveguide 16 to accommodate thermal management options. For example, the ultrasound device 10 may include a heatsink 18 that is situated in space behind the transducer 14 and is thermally coupled to the solid waveguide 16. The heatsink 18 may be defined by a skirt extending from the peripheral edges of the waveguide 16. The heatsink 18 may be integrally formed with the solid waveguide 16, or it may be separately formed and joined to the waveguide 16 during assembly of the ultrasound device 10. As another example, an active ventilation system may be incorporated into the space behind the transducer 14. The active ventilation system may include a micro-fan that moves external air through the acoustic module 12 to provide cooling. The acoustic module 12 may additionally or alternatively include a phase change material ("PCM") to help address heat. The PCM material may fill all or a portion of the space in the acoustic module 12 behind the transducer 14 and solid waveguide 16. In applications that include a heat sink, PCM material may fully or partially surround the fins of the heat sink. The PCM material may vary from application to application, but in the illustrated embodiment may be a PCM wax or a microencapsulated PCM powder.

The ultrasound device 10 may include a controller that is configured to perform a uniformity scan sweep during the application of operating power to the transducer 14. The uniformity scan sweep can be configured to extend through a frequency range that includes the operating point of the acoustic module 12 and does not exceed an acceptable efficiency loss. In some applications, the acceptable efficiency loss may be about 5%. The uniformity scan window may be determined on an acoustic module by acoustic module basis. For example, each acoustic module may be tested after production to determine the appropriate uniformity scan window for that acoustic module.

Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to any specific orientation(s).

Ultrasound Device

As noted above, the present invention is configured for incorporation into an ultrasound device, such as ultrasound device 10, which is intended for use in applying acoustic energy to human skin to address fine lines, wrinkles and sagging skin. In the illustrated embodiment, the ultrasound device 10 is a handheld device that is suitable for home use, and generally includes a power supply and the control system that are contained in a main housing 20, as well as an acoustic module 12 that is fitted to one end of the main housing 20. In this embodiment, operation of the ultrasound device 10 is controlled by a controller (not shown) that is contained in the main housing 20. The device 10 may also include a user interface that allows the user to control operation of the device 10, and allows the device 10 to provide output to the user. The user interface may vary from application to application, as desired. However, in the embodiment of FIG. 1, the user interface includes two input buttons 11a-b, three LEDs 13a-c and an OLED display 15. The user interface components may be carried on a user interface printed circuit board (not shown) that is operatively coupled to the controller. In this embodiment, the controller (not shown) is a conventional microcontroller that is configured to control all aspects of the operation of the ultrasound device 10, including controlling input from and output to the user interface, as well as controlling the supply of power to the transducer 14 in accordance with an appropriate control scheme. The controller may include or be associated with power conditioning and power control electronics that can be used to provide an appropriate electrical signal to the transducer 14. For example, the device 10 may include a driver for converting the DC signal of the power supply (e.g. batteries) to an AC signal. It may also include an amplifier for amplifying the signal as appropriate to power the transducer 14. In operation, the controller may supply operating power to the transducer 14 in accordance with an implementation of the uniformity scan method described in more detail below. The operation and control functions of the device 10 may be handled by a single controller or may be divided between multiple controllers, as desired. The control architecture of this device 10 is merely exemplary and the device may alternatively be implemented with essentially any reasonable number of separate controllers. The ultrasound device 10 may include a wireless charging system (not shown) that allows internal electrical energy storage devices to be charged using a wireless power supply, such as an inductive power supply. Alternatively, the ultrasound device 10 may include a power cord, and may receive mains power from a wall outlet. The power supplied by the power cord may be used to charge internal electrical energy storage devices so that the device is capable of cordless operation. Alternatively, the device may operate directly from main power supplied to the device by the power cord.

Generally, the acoustic module 12 of FIG. 9 contains the transducer 14, waveguide 16 and the heat sink 18. In the illustrated embodiment, the ultrasound device 10 is a portable wireless device in which the power supply is an electrical energy storage device, such as batteries or capacitors, that can be recharged and/or replaced as needed. The acoustic module 12 may include essentially any housing structure, but in the illustrated embodiment generally includes a two-piece housing assembly having a head 24 and a closure 26. The head 24 houses the transducer 14 and the solid waveguide 16. The head 24 defines a waveguide opening 28 that allows the waveguide 16 to protrude from the head 24. The closure 26 of the illustrated embodiment is configured to close the rear end of the head 24. The closure 26 may include a controller seat 27 that receives the acoustic module printed circuit board ("PCB") 22. In this embodiment, the acoustic module 12 defines an enlarged space 29 rearward of the transducer 14. As described in more detail below, this space may accommodate one or more thermal management options.

In the illustrated embodiment, the solid waveguide 16 is of a one-piece construction. The solid waveguide 16 generally includes a main body 30 having a target contact surface 32 and a transducer surface 34 disposed on opposite sides of the main body 30. In the illustrated embodiment, the target contact surface 32 protrudes from the main body 30 and is configured to be placed in direct contact with the skin of the target. In the illustrated embodiment, the shapes of the target contact surface 32 and the transducer surface 34 are selected to focus the acoustic energy. In this embodiment, the waveguide 16 is configured to apply acoustic energy along a relatively narrow line focused about 2-6 mm below the surface of the skin, but the characteristics of the focal line may vary from application to application. For example, the focal depth, the width of the focal line and the length of the focal line may be varied. To help focus the acoustic energy into a focal line, the target contact surface 32 follows a shallow curved plane. The target contact surface 32 of the illustrated embodiment is curved about a single axis. The transducer surface 34 of the illustrated embodiment is disposed on the main body 30 opposite the target contact surface 32. As with the target contact surface 32, the transducer surface 34 follows a shallow curved plane that is curved about a single axis. In this embodiment, the transducer surface 34 and the target contact surface 32 are curved about a shared axis.

In the illustrated embodiment, the acoustic module 12 includes a heatsink 18 that is affixed to the solid waveguide 16 and extends into space 29. The heatsink 18 of this embodiment generally includes two heat sink halves 18a and 18b that are affixed to opposite sides of the waveguide 16. Each heat sink half 18a-b includes a plurality of fins 40 intended to provide increased surface area to improve heat transfer. As shown, each heat sink half 18a-b extends along the inside surface of the walls of the head 24 and includes a plurality of inwardly extending fins 40. In the illustrated embodiment, the head 24 is not symmetric and the fins 40 of the two heat sink halves 18*a-b* are varied to accommodate this asymmetry. More specifically, the fins 40 of heat sink half 18*a* are substantially shorter than the fins 40 of heat sink half 18*b* so that the open space rearward of the transducer 14 corresponds with the length and width of the transducer 14. The number, size, shape and configuration of the heat sink may vary from application to application as desired. In the illustrated embodiment, the heat sink halves 18*a-b* are manufactured from aluminum, but they may be manufactured from alternative materials that provide adequate thermal mass, such as copper or brass.

To facilitate installation of the heat sink 18, the solid waveguide 16 of FIG. 1 defines a pair of heat sink slots 36*a* and 36*b*. In this embodiment, the heat sink slots 36*a-b* are relatively deep to provide greater contact area with the heat sink 18. This may help to facilitate heat transfer from the waveguide 16 to the heat sink 18. The heat sink slots 36*a-b* may also help to minimize fringe distortion waves that could have a negative impact on efficiency and performance. The heat sink 18 may be secured to the waveguide 16 using essentially any suitable method. For example, the two halves of the heat sink 18*a* and 18*b* may be secured in the heat sink slots 36*a-b*, respectively, using thermally conductive adhesive. As another example, the two halves of the heat sink 18*a-b* may be secured to the waveguide 16 by an interference fit (e.g. a press fit or friction). The size, shape and configuration of the heat sink slots 36*a-b* may vary from application to application to accommodate the desired heat sink. As described in more detail below, the waveguide 16 and heat sink 18 may be integrally formed as a one-piece component.

Figure 9A:
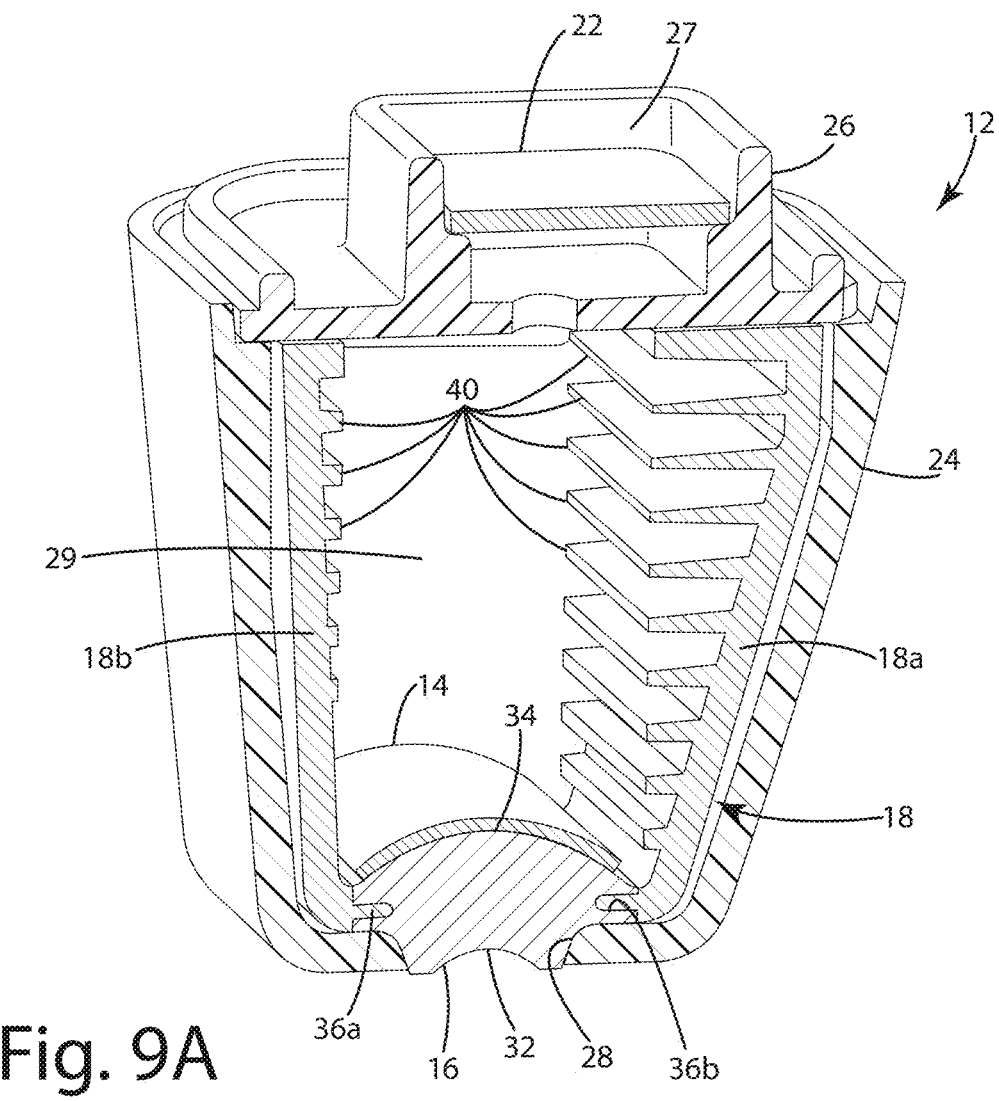
FIG. 9A is a first sectional, perspective view of the acoustic module.
Figure 9B:
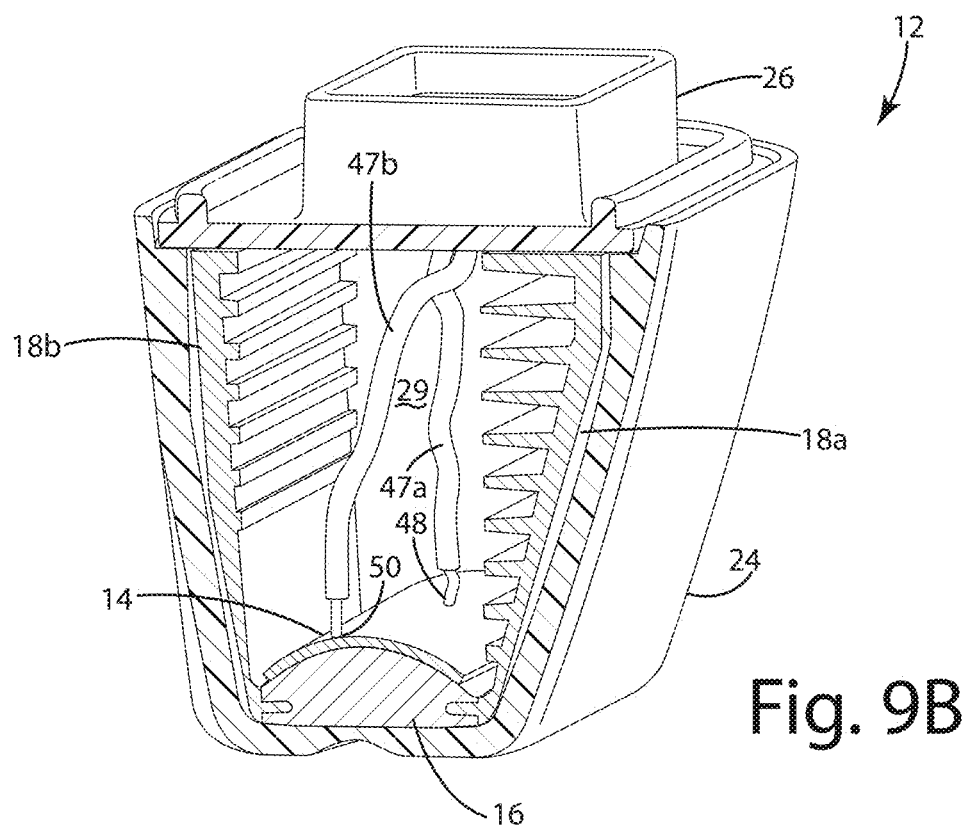
FIG. 9B is a second sectional, perspective view of the acoustic module.
Figure 10:
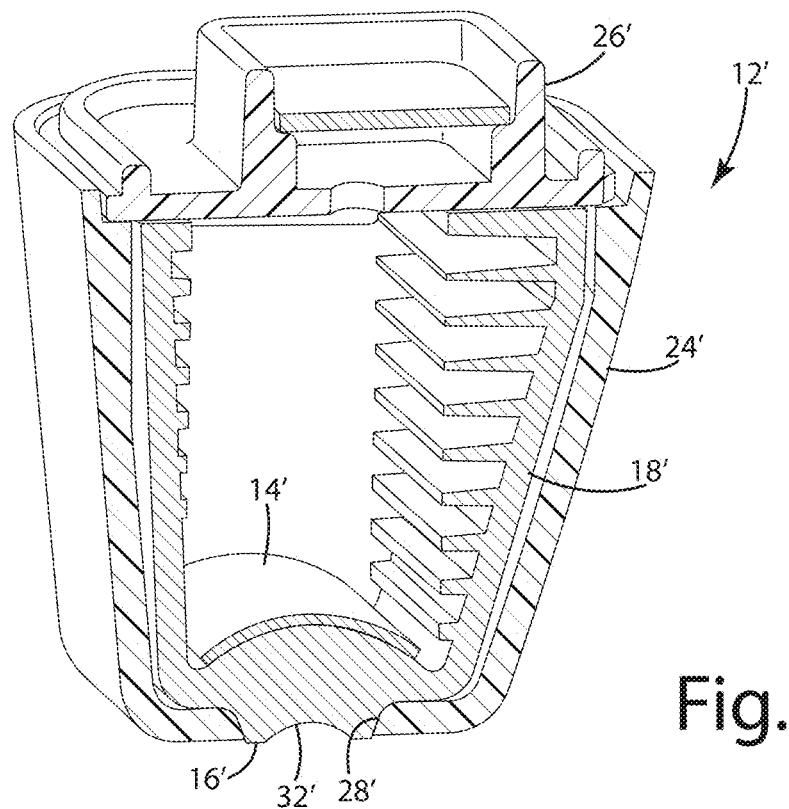
FIG. 10 is a sectional, perspective view of an acoustic module incorporating an alternative waveguide with an integral heatsink.

In alternative embodiments, the heat sink may be formed integrally with the solid waveguide. For example, FIG. 10 shows an alternative acoustic module 12' that is essentially identical to the acoustic module 12 of FIG. 9, except that the solid waveguide 16' and the heat sink 18' are of a unitary construction. As can be seen in FIG. 10, the solid waveguide 16' and heat sink 18' are enclosed within the space 29 cooperatively defined by the head 24' and the cover 26'. Like the embodiment of FIG. 9, the solid waveguide 16' extends through an opening 28' in the head 24' so that the target contact surface 32' can be brought into contact with the target.

Figure 6:
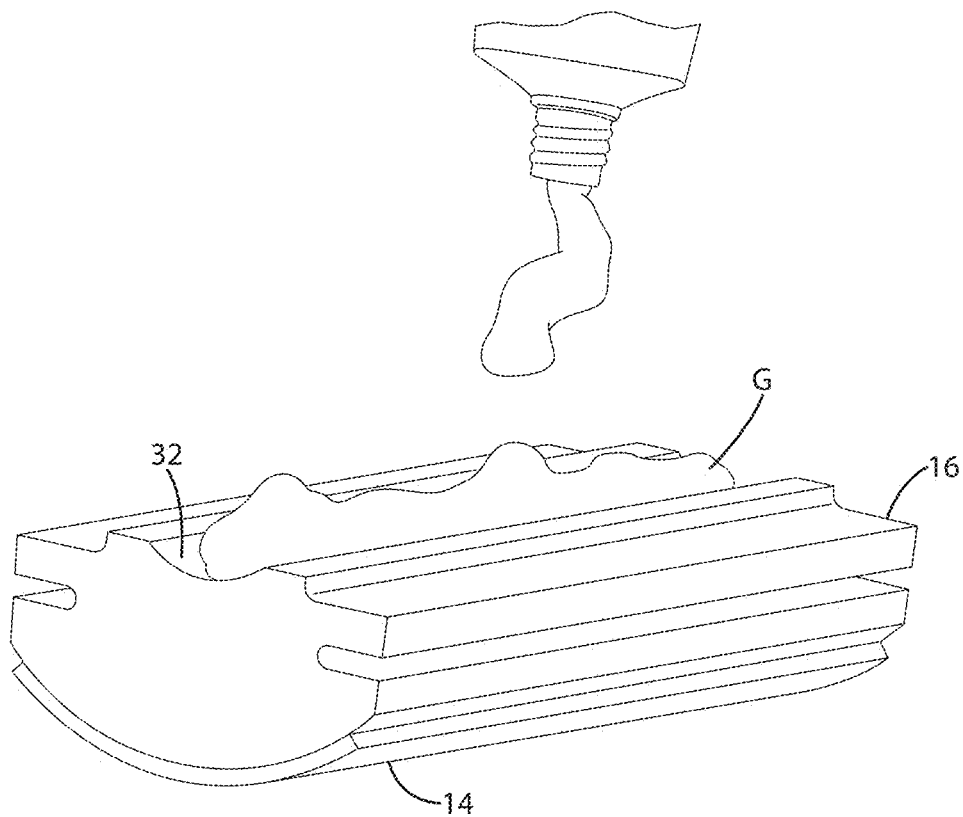
FIG. 6 is a bottom perspective view of the solid waveguide illustrating the application of ultrasound coupling gel to the target contact surface.
Figure 8:
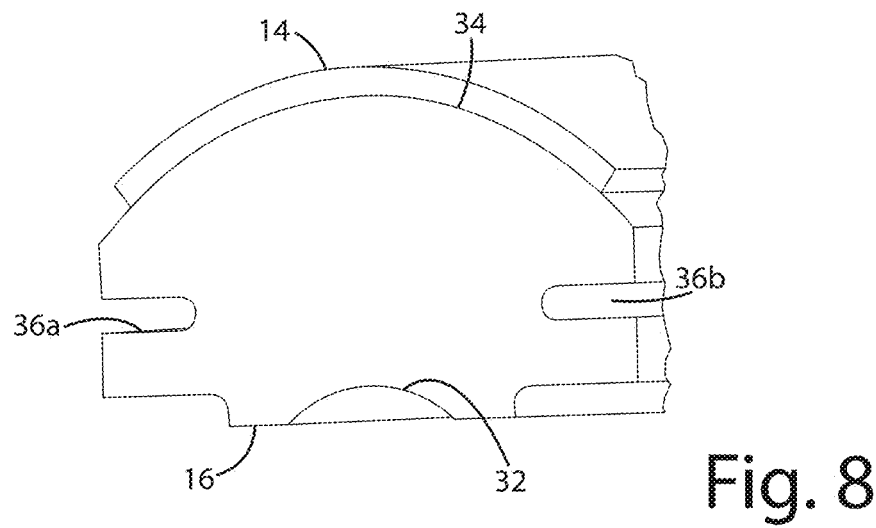
FIG. 8 is a perspective view of the waveguide illustrating electrode placement.

The geometry of solid waveguide 16 will now be described in more detail with reference to FIG. 8. As noted above, the transducer 14, target contact surface 32 and transducer surface 34 are curved to provide normal incidence to sound waves, which may improve transmission efficiency. In this embodiment, the transducer 14, target contact surface 32 and transducer surface 34 are concentric. The shape of the components may, however, be varied to mechanically change the focal depth of the acoustic module 12. For example, the surfaces 32 and 34 need not be concentric and one or more of the curves may be varied to adjust the focal depth of the acoustic module 12 (e.g. one or more of the curves may be reduced to increase the focal depth of the acoustic module 12). In this embodiment, the radial distance between the target contact surface 32 and the transducer surface 34 is selected to be approximately ½ the wavelength of the acoustic energy produced by the transducer 14 (or a multiple of ½ wavelength). As noted below, the frequency of the acoustic energy produced by the transducer 14 may vary over a range. In such applications, the thickness of the waveguide 16 may be selected to correspond with ½ wavelength or a multiple of ½ wavelength at the center of the frequency range (e.g. N×½ wavelength, where N is an integer). The heat sink slots 36*a-b* have a depth selected to approximately correspond with the longitudinal edges of the transducer 14. As noted above, this may help to minimize fringe distortion waves. The size, shape and configuration of the transducer 14 and the solid waveguide 16 may vary from application to application as desired. In the illustrated embodiment, the target contact surface 32 may be coated to facilitate contact with skin. For example, a 10-25 um layer of anodizing may be applied to the target contact surface 32 for aesthetics and biocompatibility purposes. The curved target contact surface 32 not only helps to focus acoustic energy, but it also provides a concavity to receive and hold ultrasound gel G (See FIG. 6).

Figure 18:
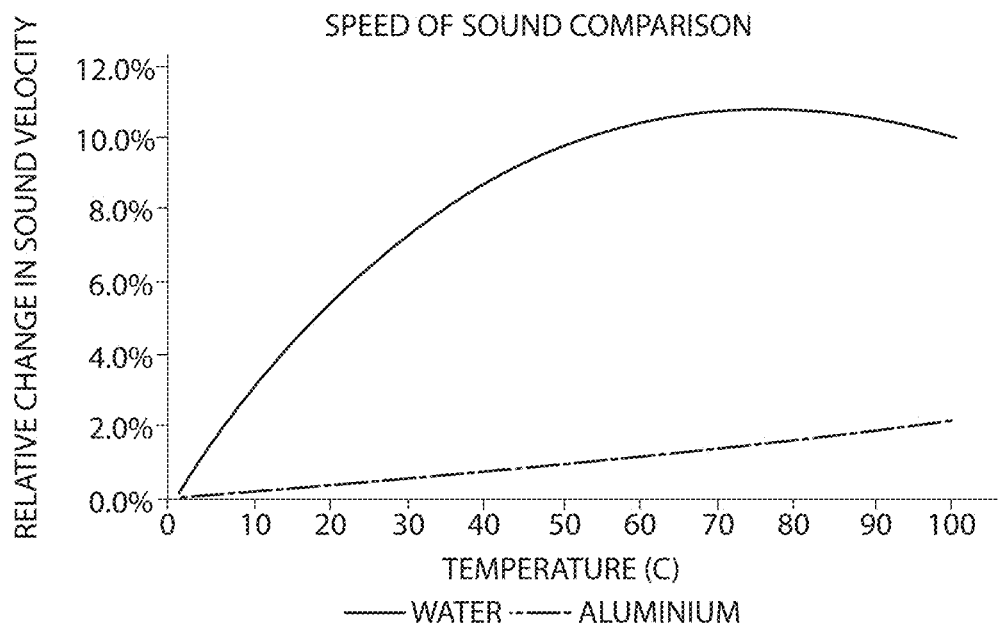
FIG. 18 is a graph comparing changes in the speed of sound against changes in temperature.

In the illustrated embodiment, the waveguide 16 is manufacture from aluminum, but it may be manufactured from other materials as desired. The waveguide 16 may be manufactured using essentially any suitable manufacturing process. For example, the solid waveguide may be extruded and cut to length or it may be machined from a block of material. As other examples, the waveguide may be die cast, investment cast or formed used metal injection molding. The waveguide may be coated, for example, with a thin film vacuum deposition layer, or anodized to prevent corrosion and surface discoloration, if desired. Although the waveguide may be manufactured from alternative materials, aluminum can be beneficial in some applications because the relationship between temperature and the velocity of sound in aluminum is substantially linear and not as significant as water. For example, as shown in FIG. 18, when considered over expected operating ranges of 20 to 40° C., the velocity of sound only changes by about 0.41% in aluminum, which is much lower than the corresponding changes in water. This translates to an 18.5 kHz shift over this temperature range. Because this is a relatively small shift from the acoustic module's overall resonant point, the system control method can be modified. With a number of conventional ultrasound devices, the controller periodically assesses the efficiency of the acoustic head at various frequencies to allow adjustment in the operating point to accommodate for changes in the internal temperature. An ultrasound device incorporating an embodiment of the present invention can target the frequency in which half standing wave cycles (or whole number multiples of a half wave) are transmitted through the aluminum waveguide. This frequency can be used as the center operating frequency for the uniformity scan control method discussed in more detail below. One benefit of this uniformity scan control method is the ability for the system to operate at a single, optimized center operating frequency without any need to shift the center operating frequency to compensate for temperature changes. This allows for a more efficient transmission of acoustic power resulting in less power consumption and heat rise by the handheld device.

Figure 4:
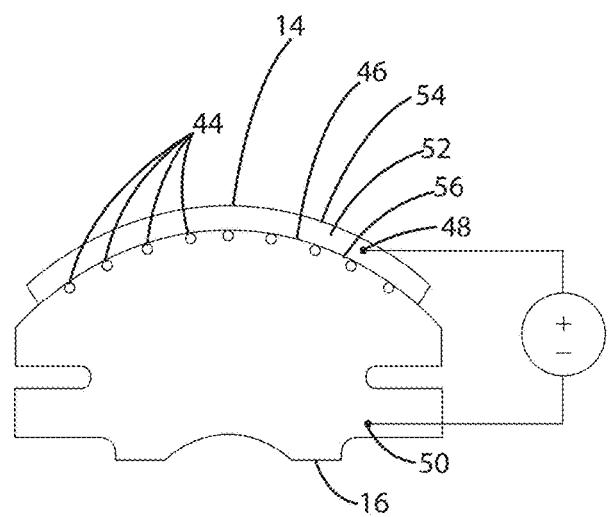
FIG. 4 is an end view of the solid waveguide.

The transducer 14 may be essentially any device exhibiting an inverse piezoelectric effect by vibrating to produce ultrasonic sound waves when subjected to an external electric field. Although the transducer 14 may vary from application to application, the transducer 14 of the illustrated embodiment includes a piezoelectric substrate 52 disposed between two conductive plates 54 and 56 (See FIG. 4). In use, the electrical drive signal is applied across the two conductive plates 54 and 56 so that electrical power passes through the piezoelectric substrate 52. In the illustrated embodiment, the transducer 14 is a piezo-electric ceramic component or a ceramic piezo crystal, such as a hard PZT of industry standard type PZT4, PZT4A, PZT4D or PZT8. For example, the transducer may be a ceramic transducer type PZT401 or PZT404 from Morgan Technical Ceramics. The conductive plates 54 and 56 may be manufactured from thick-film silver (e.g. paste with glass frit matrix) or other suitable conductive materials, such as electrodeless nickel plating. The present invention may, however, be implemented with any of a wide variety of alternative acoustic transducers that commercially available from various well-known suppliers.

Figure 2:
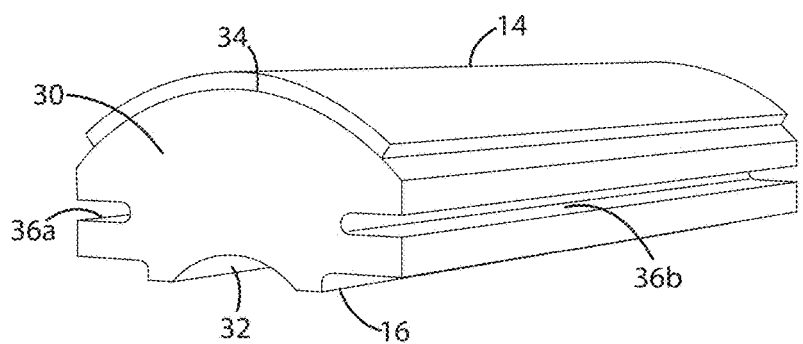
FIG. 2 is a perspective view of a solid waveguide.
Figure 7:
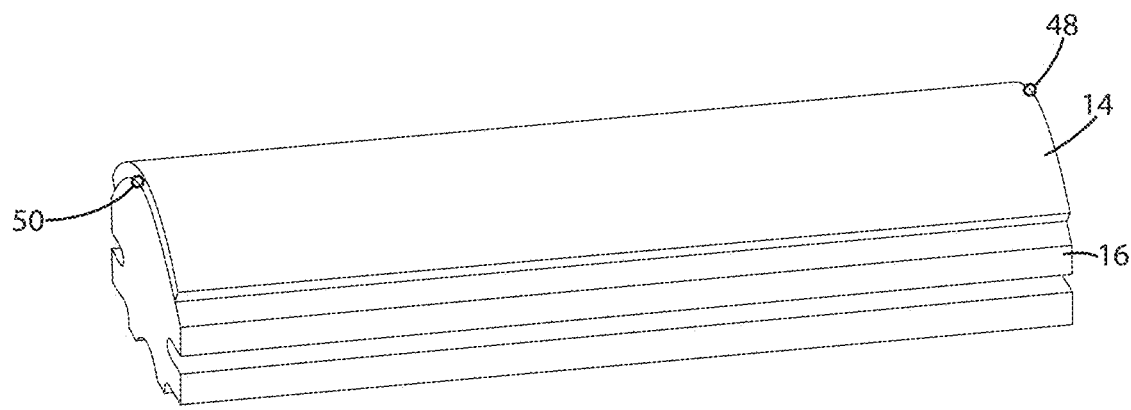
FIG. 7 is a perspective view of the waveguide.

As noted above, the transducer 14 of this embodiment is affixed to the transducer surface 34 of the solid waveguide 16. In the illustrated embodiment, the transducer 14 is secured to the solid waveguide 16 by a thin layer of epoxy 46 (or an alternative adhesive). In this embodiment, the epoxy layer 46 is relatively uniform throughout the interface between the transducer 14 and the solid waveguide 16. This can help to provide improved uniformity in acoustic energy transmission over the full extent of the target contact surface 32. When desired, the epoxy 42 may be provided with conductive beads 44 (e.g. small metal beads that are schematically represented in FIG. 2 as small circles) that provide an improved electrical connection between the transducer 14 and the solid waveguide 16. These conductive beads 44 are optional and may be eliminated when an adequate electrical connection can be established without them (or when the second electrode 50 is coupled directly to the bottom surface of the transducer 14 rather than indirectly through the waveguide 16). For example, the beads 44 may be eliminated when the epoxy or alternative adhesive is sufficiently conductive without them or when the bond line is thin enough to provide sufficient intimate/direct contact between components. In the illustrated embodiment, power is applied to the transducer 14 by a first electrode 48 that is in contact with (or otherwise coupled to) the exposed surface of the transducer 14 and a second electrode 50 that is in contact with (or otherwise coupled to) the solid waveguide 16 or the bottom surface of the transducer 14. The solid waveguide 16 is electrically coupled to the bottom surface of the transducer 14 so that, in effect, the electrical signal is applied to the top and bottom major surfaces of the transducer 14. For example, as shown in FIG. 9B, wires 47a-b may extend from the acoustic module PCB 22 to the solid waveguide 16. The first wire 47a may be joined to the top center of the transducer 14 and the second wire 47b may be joined to the top surface of the solid waveguide 16 or to conductive plate on the bottom of the transducer 14. This approach is merely exemplary, and power may be applied to the transducer 14 in alternative ways. For example, FIG. 7 shows an embodiment in which the electrodes are soldered to opposite ends of the transducer 14. In this embodiment, a first electrode is soldered to the top plate at one end longitudinal end of the transducer 14 and a second electrode is soldered to the bottom plate at the opposite longitudinal end of the transducer 14. By soldering the electrodes to opposite ends of the transducer 14, any dampening that may result from the soldered connections will have a symmetric effect on the transducer 14, thereby improving uniformity of the output acoustic field in the longitudinal direction at focus.

The type of epoxy 46 that affixes the transducer 14 to the transducer surface 34, as well as the methodology and techniques utilized for applying the epoxy 46, may vary from application to application. Example epoxies include Epotek 353ND and Epotek 301 sold by Epoxy Technology, Inc. and Loctite M-121HP sold by Loctite. In one embodiment, the type of epoxy 46 selected to bond the transducer 14 to the transducer surface 34 of the waveguide 16 may have a Shore D Hardness in the range of 70 to 90, 80 to 100, or 90 to 110 to allow for suitable transmission of ultrasound between the bonded parts. The epoxy 46 may be selected to provide sufficient bond strength to substantially ensure long term operation of the bonded components without delamination. Delamination between components (e.g., the transducer 14 and the transducer surface 34) may result in "deadzones" that can negatively impact the efficiency and uniformity measurements. The materials and processes selected to bond two components, such as the transducer 14 and the transducer surface 34, may provide substantially uniform epoxy coverage between the two components. In one embodiment, the materials and processes for applying the epoxy 46 and for bonding components may substantially prevent or avoid formation of any air pockets or voids in the bonding area. Sizable air pockets or voids may have a negative impact on the efficiency and uniformity measurements.

To ensure sufficient bond strength between the transducer 14 and the transducer surface 34 of the waveguide 16, the parts may be prepared prior to application of the epoxy 46. Preparation may include cleaning in an ultrasonic bath of isopropyl alcohol (e.g., greater than 90% pure isopropyl alcohol, or greater than 99% pure isopropyl alcohol). Additionally or alternatively, the parts may be cleaned and prepared for bonding with a plasma etch process. The plasma etch may be conducted in a vacuum chamber with plasma etching equipment, such as the Plasma Etch PE-100 sold by Plasma Etch, Inc. Alternatively, the plasma etch may be conducted under atmospheric conditions with plasma etching equipment, such as the Plasmatreat OpenAir® system sold by Plasmatreat USA, Inc.

In one embodiment, the epoxy 46 utilized to bond the transducer 14 and the transducer surface 34 of the waveguide 16 may be a two component epoxy that involves mixing and de-gassing techniques that may be specified by the epoxy manufacturer. As one example, the epoxy 46 may be manually mixed, de-gassed and loaded into a syringe for dispensing. Curing of the epoxy 46 may be accelerated by placing the parts in an oven at elevated temperatures. The bond line thickness and uniformity of the epoxy 46 may be controlled by placing a determined amount of weight or clamp force on the components being bonded during the cure process. Additionally or alternatively, an automated work cell, potentially incorporating one or more automated manipulators or robotic components, may be provided to plasma etch parts, mix epoxy, dispense epoxy, join the parts, provide clamp force and feed them into a conveyor oven for curing. According to one embodiment, dispensing of epoxy may utilize a dispensing valve, such as one of the dispensing valves offered by PVA or Precision Valve & Automation, including the DX100 and VPX-2k dynamic mixing valves sold by PVA. The clamping force applied in bonding components according to one embodiment may be greater than or substantially equal to 1 lb., 3 lbs. or 5 lbs. Oven temperatures for curing the epoxy 46 may vary from application to application, depending on the type of epoxy 46 and the materials involved. As an example, the oven temperature may be set for operation between 90 C-95 C, 95 C-100 C, 100 C-105 C, 105 C-110 C, or 100 C-110 C. The duration of curing may also vary from application to application, including curing for greater than or substantially equal to 6 min, 12 min., 18 min., 24 min., and 30 min.

Figure 3:
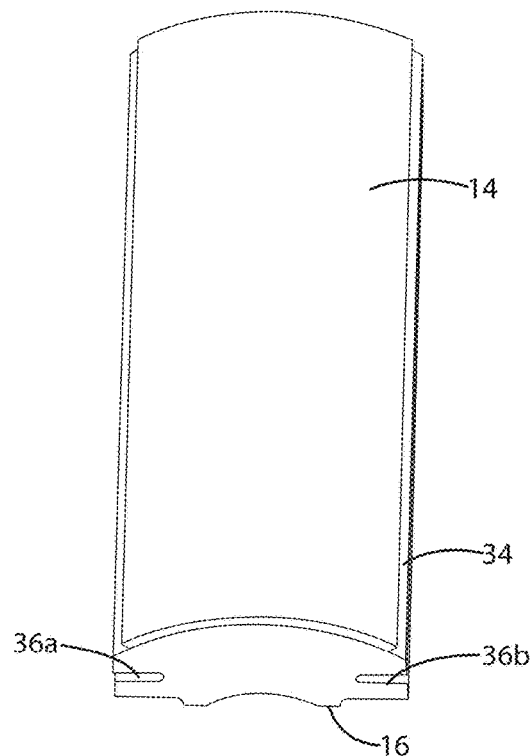
FIG. 3 is a top view of the solid waveguide.

Experience has revealed that maintaining proper placement of the transducer 14 on the solid waveguide 16 can provide improved uniformity in acoustic transmission and improved consistency from product to product. In alternative illustrated embodiment, the solid waveguide 16 may include an epoxy "frame" that is configured to help hold the transducer 14 in place on the waveguide 16 (See FIGS. 2 and 3). In this alternative embodiment, the epoxy frame includes narrow ridges of epoxy that extend upwardly from the transducer surface 34 just outside the peripheral edges of the transducer 14. These ridges may result from the process of securing the transducer 14 to the solid waveguide 16. More specifically, the ridges may be formed by extra epoxy that oozes out from between the transducer 14 and the solid waveguide 16 when the transducer 14 and waveguide 16 are placed together over uncured epoxy. If desired, the transducer surface 34 of the waveguide 16 may be configured to assist in forming the epoxy ridges. For example, the transducer surface of the waveguide 16 may include small ribs that are spaced apart from the peripheral edges of the transducer 14 to help accumulate and shape epoxy oozing from between the transducer 14 and the waveguide 16. The epoxy ridges extend completely around the periphery of the transducer 14 or they may extend along only portions of the periphery.

Figure 5:
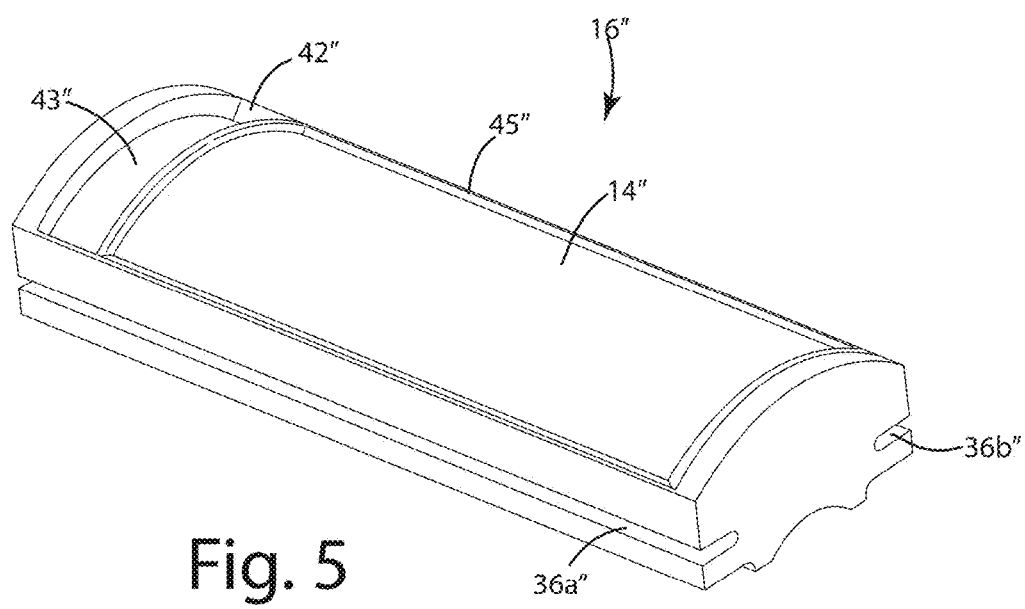
FIG. 5 is a perspective view of an alternative solid waveguide.

The transducer may be secured to the waveguide using other techniques and apparatus. For example, in an alternative embodiment shown in FIG. 5, the solid waveguide 16" may be provided with a transducer seat 42". The transducer seat 42" may be a shallow recess in the transducer surface 34 configured to closely correspond with the peripheral shape of the transducer 14". The recess may help to properly position and hold the transducer 14" in place on the waveguide 16". Electrical contacts can be applied to the transducer 14" in a variety of alternative ways. In this embodiment, the transducer 14" includes a piezoelectric substrate that is sandwiched between a pair of conductive plates. More specifically, the exposed major surface of the transducer 14" may be the first conductive plate and the hidden major surface may be the second conductive plate. To provide an electrical signal to this transducer 14", the device may include a first electrical contact, such as a spring loaded contact (e.g. pogo pin) (not shown), that is in direct contact with the top surface of the transducer 14". For example, the pogo pin may be in contact with the approximate center of the first conductive plate on the exposed surface of the transducer 14". As shown in FIG. 5, the transducer seat 42" may be longer than the transducer 14" to provide an extension portion 43" that can receive an electrical contact. For example, a second electrical contact, such as a spring loaded contact (e.g. pogo pin) (not shown), may be positioned in the extension portion to connect the power signal to the solid waveguide 16". The solid waveguide 16" may be electrically coupled to the second conductive plate on bottom surface of the transducer 14" by electrically conductive adhesive. In the embodiment of FIG. 5, a narrow strip of epoxy may form a "frame" 45" around the transducer 14". In this embodiment, the transducer seat 42" may be slightly larger than the transducer 14" so that there is a narrow gap between the periphery of the transducer 14" and the transducer seat 42". During assembly, epoxy applied between the transducer 14" and the solid waveguide 16" may ooze out from between the components and form the illustrated epoxy frame 45". The use of an epoxy frame is optional and may be eliminated when not desired.

Figure 11:
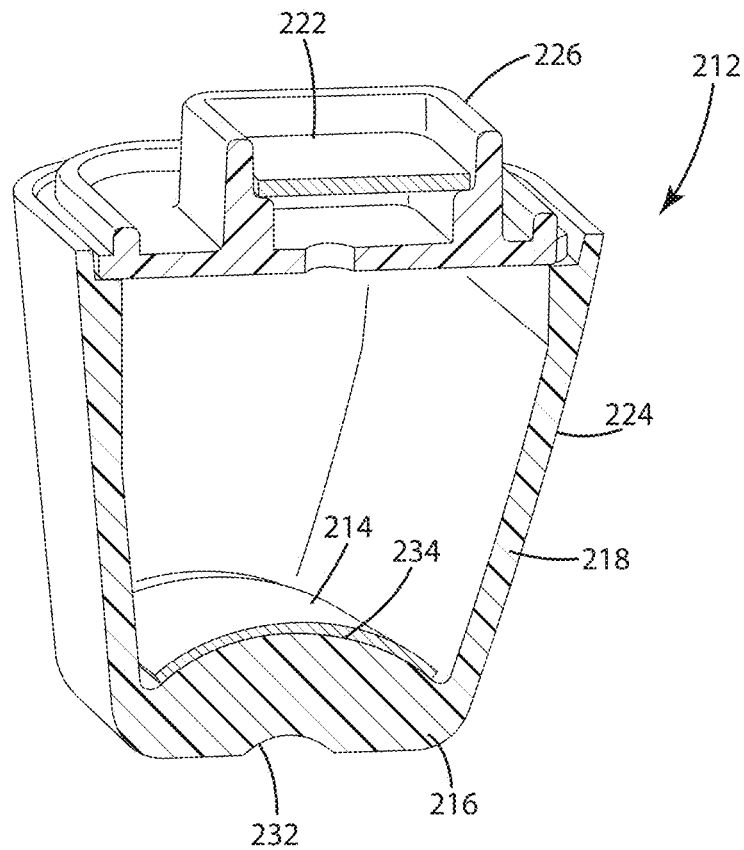
FIG. 11 is a sectional, perspective view of an acoustic module incorporating a further alternative embodiment.

In an alternative embodiment of the acoustic module 212, the solid waveguide 216 and heat sink 218 may be of a unitary construction. As shown in FIG. 11, the heat sink 218 may be in the form of a skirt extending rearwardly from the peripheral edges of the solid waveguide 216. The rearward end of the heat sink 218 may be closed by cover 226. In this embodiment, the solid waveguide/heat sink combination may itself form the head 224 of the acoustic module 212, thereby eliminating the use of a separate housing component to form the head 24 as illustrated in FIG. 9A. As shown, the transducer 214 may be secured to the transducer surface 234 of the solid waveguide 216 in essentially the same manner as shown in connection with the embodiment of FIG. 1.

Figure 12:
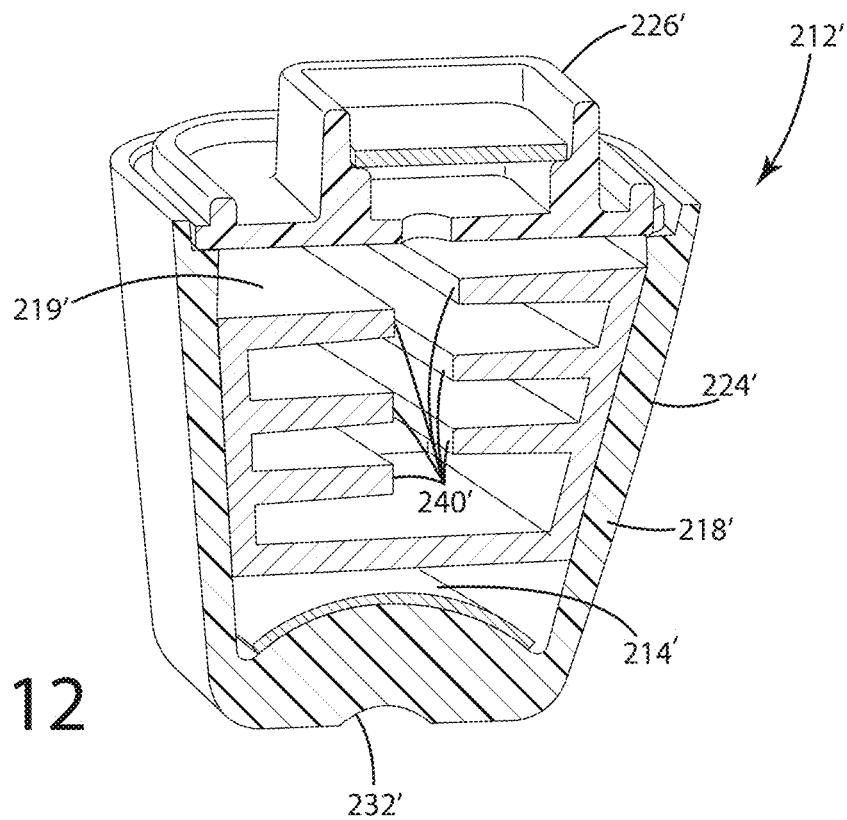
FIG. 12 is a sectional, perspective view of an acoustic module incorporating another alternative embodiment of the present invention.

In this embodiment, it may be desirable to provide supplemental thermal management. For example, as shown in FIG. 12, the acoustic module 212' may include a supplemental heat sink 219' that is disposed within the interior of the acoustic module 212'. The supplemental heat sink 219' may be in direct contact with the skirt 218' and may include a plurality of fins 240' that increase surface area and thereby improve thermal transfer. The size, shape and configuration of the heat sink 219' may vary from application to application as desired. As another option, the skirt may itself include a plurality of integral fins to provide improved heat transfer without the need for a separate heat sink (not shown).

Figure 13:
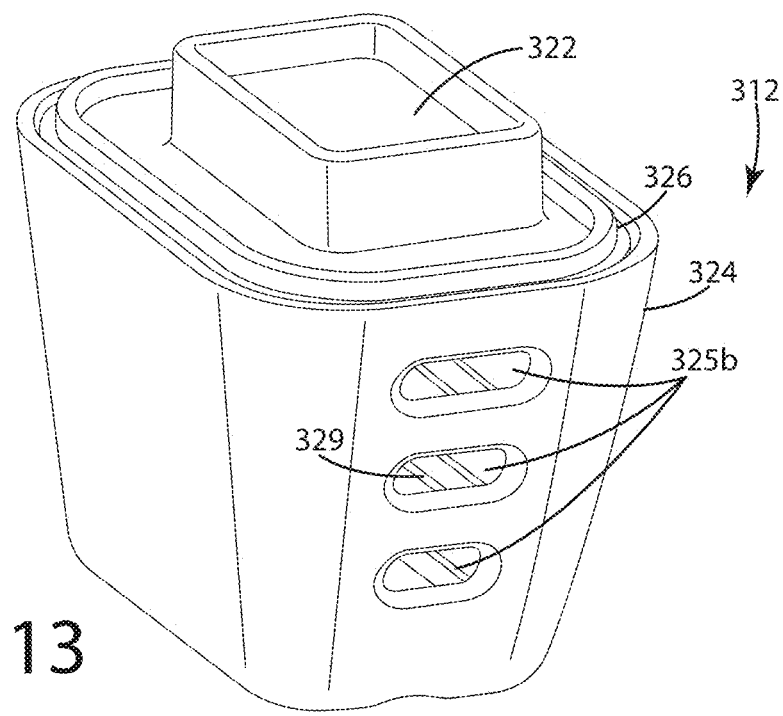
FIG. 13 is a perspective view of the vented acoustic module.
Figure 14:
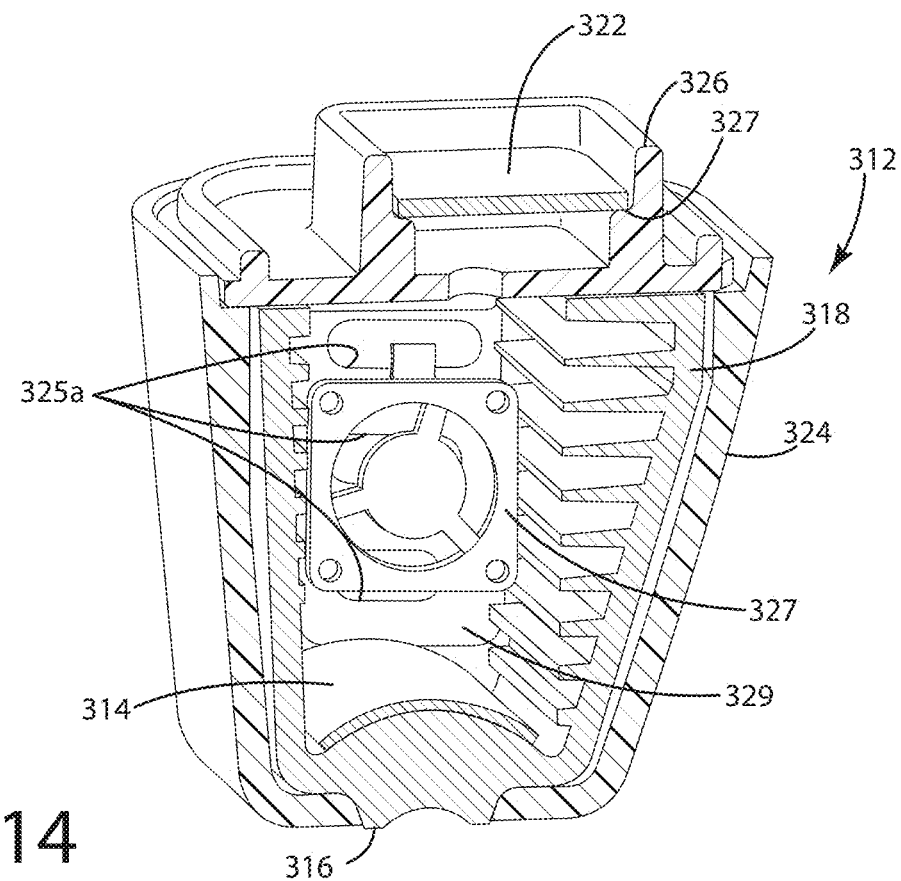
FIG. 14 is a sectional, perspective view of a vented acoustic module.

In another alternative embodiment, the acoustic module 312 may be provided with an active ventilation system (See FIGS. 13 and 14). In this embodiment, the head 324 includes ventilation openings 325*a-b* and an internal fan 327 for moving air through the acoustic module 312. In the illustrated embodiment, the head 324 defines two sets of ventilation openings 325*a-b* in opposed sidewalls, with one set of ventilation openings 325*a* cooperatively providing an air outlet and the other set of ventilation openings 325*b* cooperatively providing an air inlet. FIG. 14 shows outlet openings 325*a* and FIG. 13 shows inlet openings 325*b*. The number, size, shape and position of ventilation openings may vary from application to application. The ventilation openings 325*a-b* may be covered by an air permeable membrane 329 that prevents water and debris from entering the acoustic module 312 through the ventilation openings 325*a-b*. The air permeable membrane 329 may be replaced by other ventilation materials, such as perforated materials and other air permeable materials. For example, the ventilation openings may be cover by open cell foam, filter media and/or by a layer mesh/screen with small openings. Referring now to FIG. 14, the internal fan 327 may be a low power micro fan. A variety of suitable alternative fans are commercially available from various well-known suppliers. In use, the fan 327 may draw cool air into the acoustic module 312 through the inlet openings 325*b*, move the air over the heat sink 318 and heat sink fins 340 and discharge the air through the outlet openings 325*a*. If desired, the acoustic module 312 may be provided with a temperature sensor (not shown) and the controller (not shown) may be configured to operate the fan 327 only when the temperature within the acoustic module 312 exceeds a predetermined threshold.

Although the active ventilation system is described in connection with an acoustic module that is essentially identical to acoustic module 12', it should be understood that the active ventilation system may be incorporated into essentially any of the alternative acoustic modules shown or described herein.

The various acoustic modules shown in FIGS. 9-14 are configured with the transducer affixed directly to the solid waveguide. In alternative embodiments, a lens may be disposed between the transducer and the waveguide. For example, FIG. 17 shows an alternative embodiment in which the acoustic module 412 includes a lens 460 and a waveguide 416. In this embodiment, the transducer 414 is a planar piezo ceramic crystal (though it could be other types of transducers). The lens 460 of this embodiment is manufactured from aluminum and has a planar transducer surface 433 that receives the transducer 414 and a curved waveguide surface 435 that interfaces with the waveguide 416. The curvature of waveguide surface 435 is configured to match with the curvature of the lens surface 434 of the waveguide 416 to provide an intimate and uniform connection over the entire interface region. The curved surfaces along the acoustic pathway are selected to provide the desired focus to the acoustic energy. For example, the curvature of the lens and waveguide are selected to focus the acoustic energy at a depth of approximately 2-6 mm from the target contact surface 432. Although the waveguide 416 of this embodiment is manufactured from cross-linked polystyrene, (e.g. Rexolite® plastic), the waveguide 416 may be manufactured from alternative materials. For example, the waveguide 416 may be manufactured from cyclic olefin copolymer, silica or borosilicate (e.g. Pyrex®). The transducer 414 may be secured to the lens 460 using a thin layer of epoxy (not shown). In this embodiment, a first electrode (not shown) is electrically coupled to the top, exposed surface of the transducer 14 and a second electrode (not shown) is electrically coupled to the bottom surface of the transducer 14. In this embodiment, the lens 460 includes a small groove 461 (or other recess) that provides access to the bottom surface of the transducer 14. The second electrode can be routed to the bottom surface of the transducer 14 via the groove 461. As an alternative, the second electrode can be electrically coupled to the lens 460 and the lens 460 may be electrically coupled to the bottom surface of the transducer 414. For example, as discussed above, the epoxy may include conductive beads that provide an electrical connection between the lens 460 and the bottom surface of the transducer 414.

The waveguide 416 is disposed below the lens 460 and is configured to transmit acoustic energy received from the lens 460. In this embodiment, the waveguide 416 is essentially identical to the solid waveguide 16, discussed above. As a result, waveguide 416 will not be described in great detail. The waveguide 416 includes a curved upper waveguide surface 435 that is secured to the lens surface 434 of lens 460. In this embodiment, the lens 460 is secured to the waveguide 416 by a thin layer of epoxy or other suitable adhesive. The waveguide 416 of this embodiment is manufactured from plastic having appropriate sound transmission characteristics (e.g. acoustic impedance). For example, waveguide 416 may be manufactured from Rexolite® high performance plastic.

The material of the lens and waveguide may vary from application to application. However, it may be desirable in some applications for the materials to be selected to provide an acoustic pathway with decreasing acoustic impedance. This may improve transmission of acoustic waves through the delay path. With the embodiment shown in FIG. 17, the transducer 414 has an acoustic impedance of about 34MRayls, the aluminum lens 460 has an acoustic impedance of about 17MRayls and the Rexolite® plastic waveguide 416 has an acoustic impedance of about 2.3MRayls. These values are approximate and some variations may occur due to variations in material properties.

Phase Change Materials

During operation, the transducer 14 may generate a significant amount of thermal energy. In some applications, it may be desirable to provide thermal management components to help absorb thermal energy so that the waveguide or any other skin-contact components do not reach a temperature deemed to be uncomfortable (e.g. approximately 40 C). As described above, thermal management may be provided by various heat sink arrangements and/or by an active ventilation system. In supplement or as an alternative to other thermal management options described herein, the acoustic module may be provided with phase change materials that absorb and storing heat generated by the transducer.

For purposes of disclosure, the incorporation of phase change materials is described in connection with a waveguide/heat sink component shown in FIG. 15. This waveguide/heat sink component is essentially identical to the waveguide/heat sink 16', 18' of FIG. 10, but phase change materials may be incorporated into essentially any acoustic module having a space capable of receiving the phase change material. In the embodiment of FIG. 15, the waveguide 516 and heat sink 518 are integrally formed as a one-piece component. In this embodiment, the phase change material 570 is configured to partially or completely fill the internal space in the acoustic module 522. In use, the phase change material 570 is in contact with the fins 540 of the heat sink 518 to increase the surface area of thermal transfer.

The amount of phase change material incorporated into the acoustic module 520 may be determined based on the specific application. For example, one method for determining the amount of phase change material in the illustrated embodiment will now be described. In this example, it has been determined that upper temperature threshold for the device is 40 degrees C. The 40-degree threshold is merely exemplary, and the threshold may vary from application to application. With this threshold, it is desirable to incorporate a phase change material with a thermal mass that is sufficient to prevent the device from exceeding 40 degrees C. under normal circumstances. In the illustrated embodiment, the acoustic module 520 generates approximately 1 W of thermal energy when it is used for less than 3000 s. This was determined through testing of the device. As a result, with this embodiment, a thermal mass with sufficient heat capacity to absorb 3 kJ without exceeding a threshold of 40 degrees C. is suitable. In use, the present invention takes advantage of the phase change of a thermal absorber. For purposes of this example, the phase change material will be paraffin wax, which has a latent heat of fusion of 190-200 J/g). This means that 16 g of the material could absorb the full 3 kJ without a significant change in temperature if it is at the melting point. Since the heat capacity of the material is much lower away from melting point (SHC ~2.5 J/(g*degC)), a melting temperature of approximately 37 C was selected so that if there was a fully melted scenario there would still be a few degrees to rise before hitting the threshold. FIG. 16 is a graph showing the internal temperature of the acoustic module over time during a full treatment period. As can be seen, the internal temperature does not exceed the 40 degrees C. maximum threshold. After use, the liquid or semisolid wax would then be allowed to fully cool back to ambient temperature slowly throughout the day. If desired, the controller can be configured to prevent operation of the device until the phase change material has had an opportunity to adequately cool. In the illustrated embodiment, this is enforced by software on the device that prevents use of the device more often than might allow full heat capacity to be restored. The acoustic module 520 may include a temperature sensor (not shown) that allows the controller to prevent operation of the device until the device has cooled below an operating threshold. Alternatively, the software may be configured to operate based on time. For example, the system may be programmed with a cool-down time period that must pass between uses of the device.

In the illustrated embodiment, the phase change material is in the form of paraffin wax, which has a latent heat of fusion of about 190-200 J/g. In use of the illustrated embodiment, 16 g of paraffin wax will generally be capable of absorbing all of the thermal energy that will be generated by the transducer 14 during a single use without exceeding 40 degrees C. Because it is possible for the paraffin wax to fully melt, it may be desirable to contain the wax, and potentially to keep the liquid wax off of the face of the transducer. This can be accomplished by using a rigid box that holds the material, creating a shelf that defines an enclosed space within the heat sink cavity, or by encapsulating the phase change material in a flexible pouch or bag. Alternatively, a foam tape such as 3M's VHB could be placed on the transducer to acoustically isolate the transducer from the molten or solid PCM.

In alternative embodiments, the present invention may be implemented with essentially any phase change material. For example, the phase change material may be in the form of a microencapsulated powder or a macroencapsulated gel. As with paraffin wax, any of these alternative phase change materials may be contained within some form of enclosure, such as a box, flexible bag, shrink wrap or rigid enclosure. In some applications, the acoustic module may include a combination of different phase change materials. In one alternative embodiment, the phase change material may be a "microencapsulated" PCM powder, such as MPCM 37D from Microtek Industries of Dayton, Ohio. This material includes the phase change liquid that converts from solid to liquid at a temperature of approximately 37 degrees C., but is held in a small shell of a high melting point polymer. The net effect is a flowing powder that can be packed around the heat sink fins to absorb heat that will stay in its powdery form through the anticipated temperature range of consumer electronics. To increase the powder packing density and shorten fill time, a vibration table can be used. In the illustrated embodiment, the microencapsulated PCM powder is in direct contact with the piezoelectric crystal, and there is enough thermal conductivity (but sufficiently small acoustic coupling such that system efficiency is minimally affected) that no additional heat piping structures is needed.

In other alternative embodiments, the acoustic module may be provided with phase change materials that operate using different types of phase changes. For example, phase change materials that undergo a solid/solid recrystallization may be utilized for thermal management. Phase change materials of this type are commercially available from Phase Change Material Products Ltd in Yaxley, UK. These materials offer the ability to absorb heat at a constant temperature in a very similar manner to the liquid/solid PCMs previously described. These materials are often coated with a wax or polymer barrier.

Alternative Embodiments

As noted above, the design and configuration of the acoustic module may vary from application to application, as desired. As an illustration, another alternative ultrasound device 610 will now described with reference to FIGS. 22-25. This alternative embodiment of the present invention is essentially identical to embodiment of FIGS. 1-4 and 6-9, except for variations in the acoustic module 612 as described below and shown in the drawings. To facilitate disclosure, ultrasound device 610 will be described using reference numerals that correspond with those used in connection with ultrasound device 10, except that they will be preceded by the number "6" in the hundreds place. For example, ultrasound device will be designated by reference numeral 610 (rather than 10), the acoustic module will be designated by reference numeral 612 (rather than 12) and the solid waveguide will be designated by reference numeral 616 (rather than 16).

Figure 23:
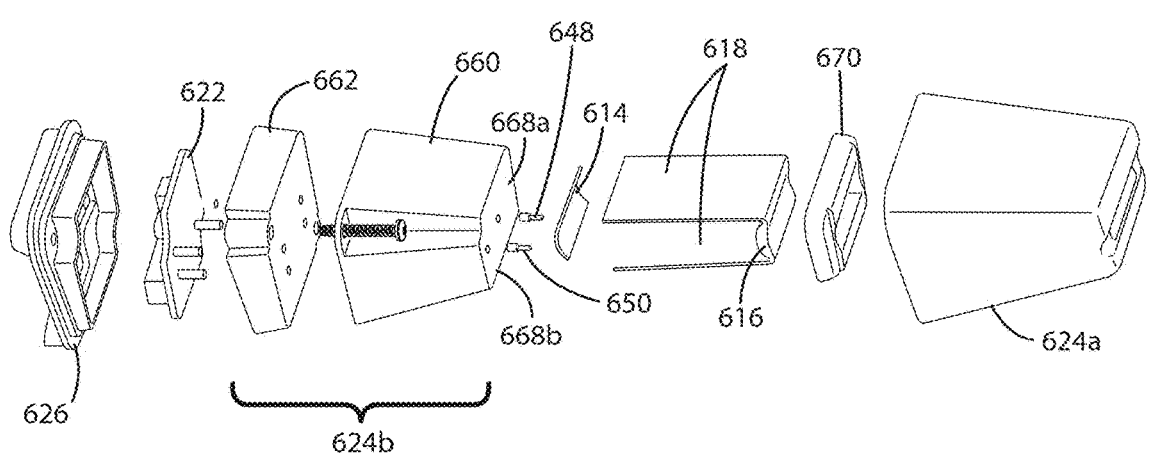
FIG. 23 is an exploded perspective view of the acoustic module of the ultrasound device of FIG. 22.
Figure 24:
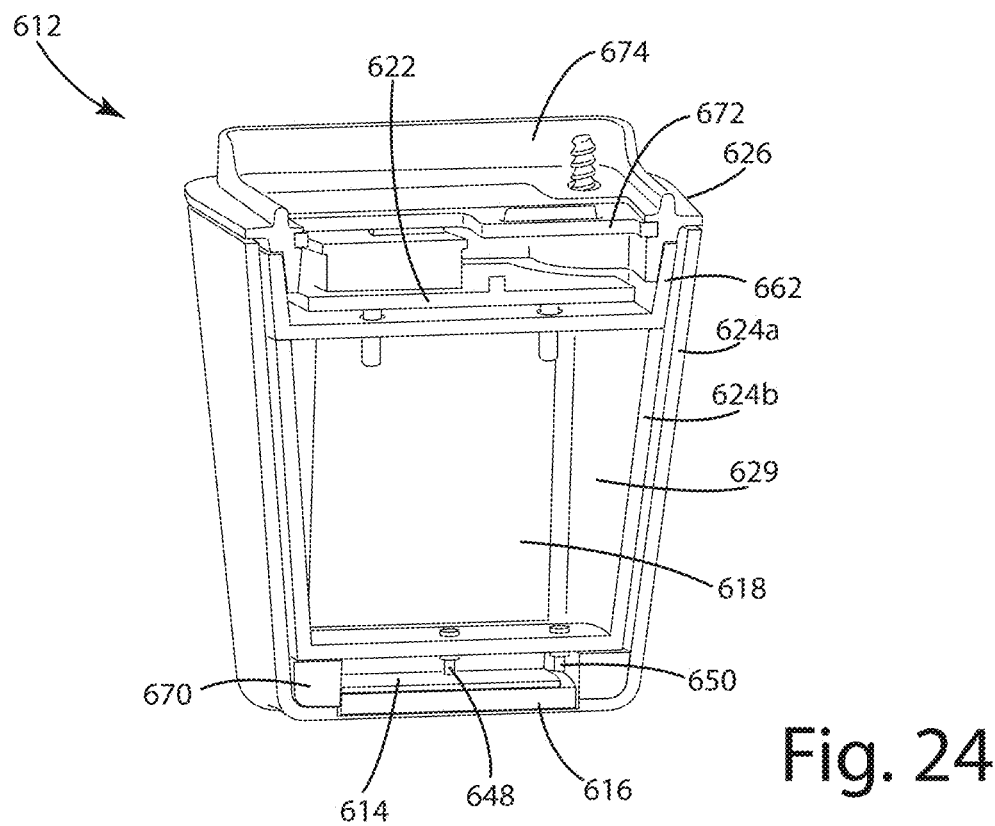
FIG. 24 is a sectional view of the acoustic module taken along line 24-24 of FIG. 22.

Ultrasound device 610 differs from ultrasound device 10 primarily in connection with variations in the acoustic module 612. Referring now to FIG. 23, the acoustic module 612 of ultrasound device 610 generally includes an outer housing 624a, an inner housing 624b and a cover 626. The outer housing 624a may be generally identical to housing 24 shown in the embodiment of FIG. 9. The inner housing 624b may include main portion 660 and a closure 662. The main portion 660 and closure 662 cooperatively define an internal space 629 configured to receive the heat sink 618. Although not shown, the internal space 629 may also include a phase change material (as described above) to provide supplement thermal management. For example, sufficient phase change material may be inserted into the inner housing 624b to fill the unoccupied regions within the internal space 629. In this embodiment, the solid waveguide 616 and heat sink 618 are formed integrally as a one-piece component. Unlike heat sink 18, heat sink 618 of this embodiment does not include fins. To allow the heat sink to be situated within the internal space 629 and the solid waveguide 616 and transducer 614 to be situated outside the internal space 629, the main portion 660 defines a pair of slots 668a-b that allow the heat sink 618 to be fitted into the internal space 629 in the inner housing 624b (See FIG. 25). The cover panel 662 can be installed on the open end of the inner housing 624b. In this embodiment, the transducer 614 is disposed on the solid waveguide 616 adjacent the inner housing 624b. As with previously described embodiments, the transducer 614 may be affixed to the solid waveguide 616 by an electrically conductive adhesive. The transducer 614 may be shorter than the solid waveguide 616 so that a portion of the top surface of the solid waveguide 616 is exposed. As show, electrical contact may be made by a pair of pogo pins 648 and 650 (or other electrical contacts, such as other spring loaded contacts) that are mounted in the inner housing 624b. For example, pogo pins 648 and 650 may be secured to the inner housing 624b by adhesive or by an interference fit. Pogo pin 648 may be in contact with the approximate center of the top surface of the transducer 614. Central positioning of pogo pin 648 may facilitate uniform acoustic transmission. Pogo pin 650 may be in contact with the exposed portion of the solid waveguide 616, which is in turn in electrical contact with the bottom surface of the transducer 614. Although not shown, the pogo pins 648 and 650 may be electrically coupled to the acoustic module PCB 622 by electrical leads routed through the internal space 629. As an alternative to pogo pins or other connectors, electrical leads can be soldered or otherwise operatively secured to the conductive plates of the transducer 614.

In this embodiment, a gasket 670 may be situated between the outer housing 624a, inner housing 624b and solid waveguide 616. The gasket 670 may be configured to fit tightly between the various components to help prevent water from infiltrating into the acoustic module 612. The gasket 670 may be rubber or other suitably resilient gasket material. In alternative embodiments, the gasket 670 may be eliminated or may be replaced by a form-in-place or cure-in-place gasket material.

In the illustrated embodiment, the cover 626 generally includes a structural element 672 and a resilient overmold 674. The structural element 672 may define an opening 678 to allow wiring or other electrical conductors to be routed between the controller (not shown) and the acoustic module PCB 622. The overmold 674 may be formed about the periphery of the structural element 672 to help provide a leaktight seal between the main housing 620 and the acoustic module 612. As shown, the overmold 674 may include a lip 676 that is sandwiched between the main housing 620 and the outer housing 624a. Although molded directly onto the structural element 672 in this embodiment, the overmold 674 may alternatively be replaced by a separately manufactured gasket or seal component.

Figure 25:
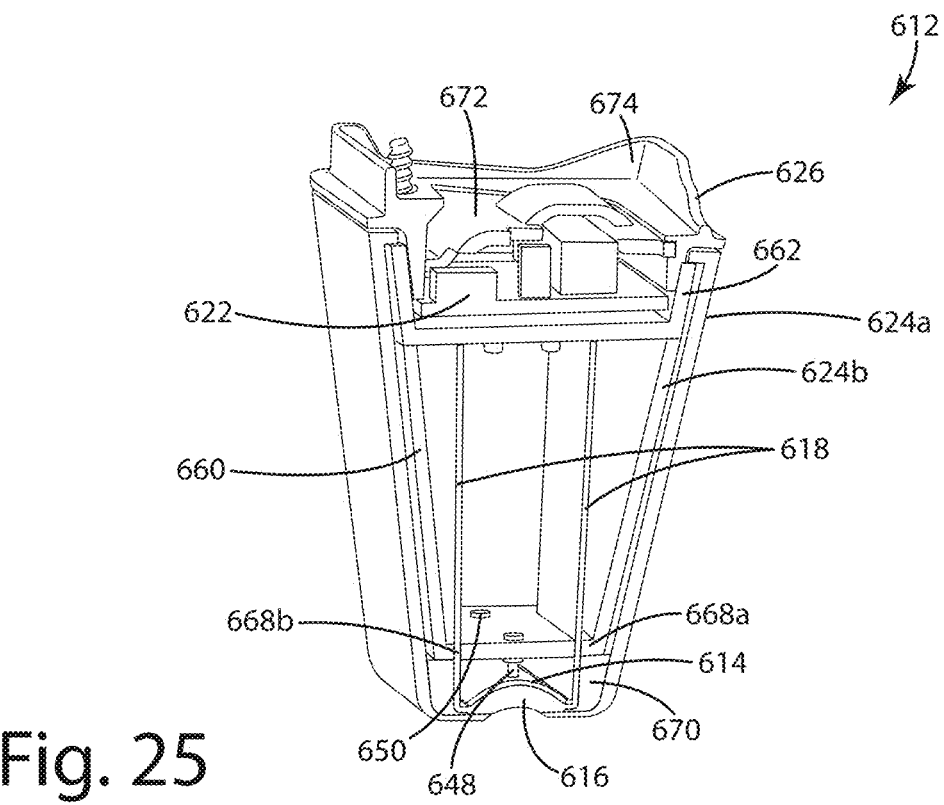
FIG. 25 is a sectional view of the acoustic module taken along line 25-25 of FIG. 22.

As noted above, the cross-sectional shape of the solid waveguide may vary from application to application. In the embodiment of FIGS. 22-25, the solid waveguide 616 may have a somewhat different shape than solid waveguide 16. As shown in FIG. 25, solid waveguide 616 may be thinner and may not include a protruding contact surface 632. Instead, the solid waveguide contact surface 632 may be disposed inwardly of the outer housing 624a, and the outer housing 624a may be shaped to provide a shallow concavity that complements the shape of the contract surface 632.

Figure 26:
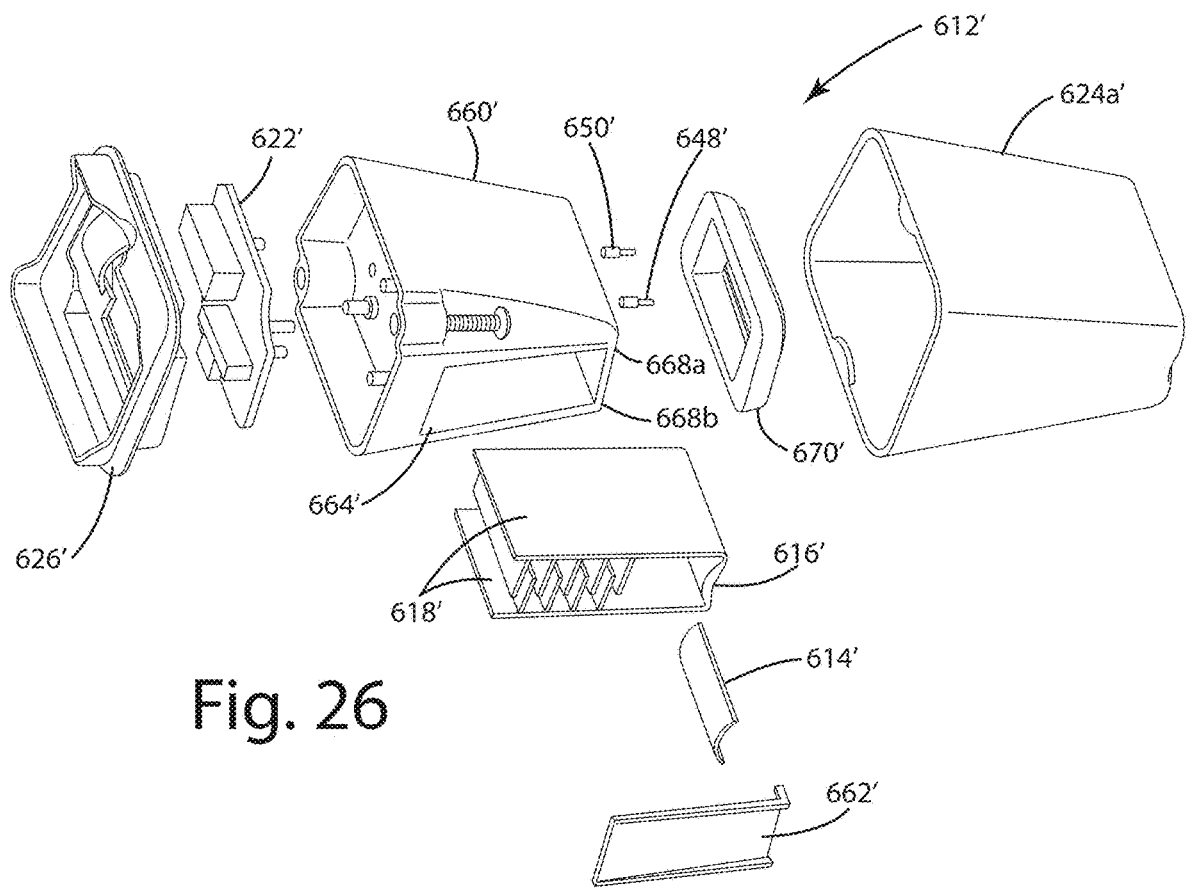
FIG. 26 is an exploded perspective view of an alternative acoustic module.
Figure 27:
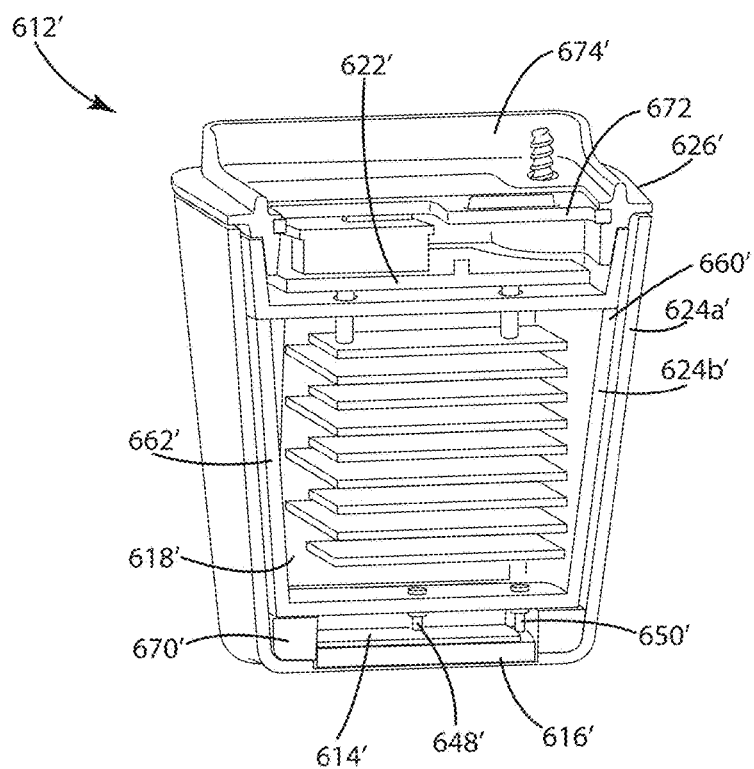
FIG. 27 is a first sectional view of the alternative acoustic module of FIG. 26.
Figure 28:
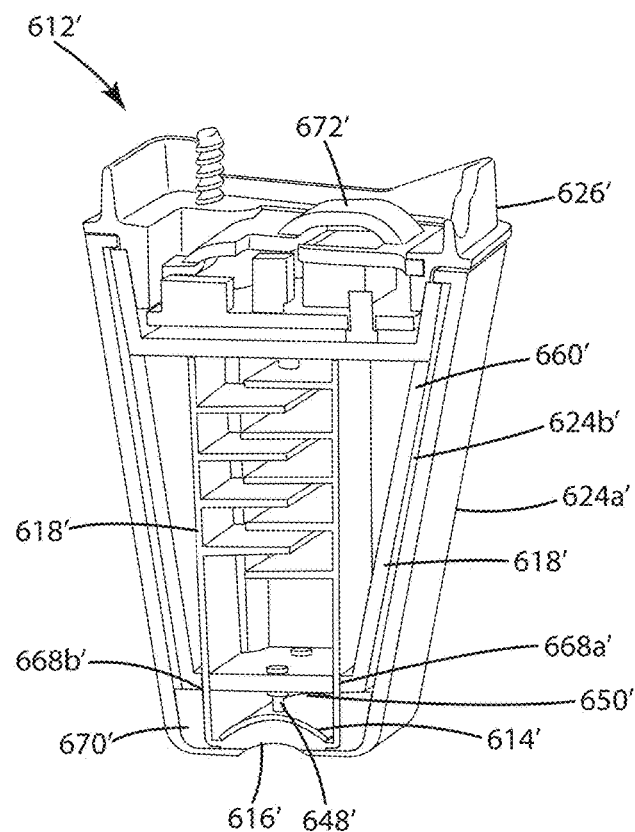
FIG. 28 is a second sectional view of the alternative acoustic module of FIG. 26.

An alternative embodiment of the acoustic module 612' is shown in FIGS. 26-28. In this embodiment, the acoustic module 612' is generally identical to acoustic module 612, except with respect to variations in the heat sink and inner housing as described and shown. Acoustic module 612' will be described using reference numerals that correspond with those used in connection with ultrasound device 610, except that they will be followed by the prime symbol. For example, the acoustic module will be designated by reference numeral 612' (rather than 612) and the solid waveguide will be designated by reference numeral 616' (rather than 616). In this embodiment, the solid waveguide 616' and heat sink 618' are formed as a single unitary component. For example, the solid waveguide 616' and heat sink 618' may be extruded from aluminum as a single, one-piece extrusion. The heat sink 618' may include a plurality of fins 640' that increase heat transfer surface area and therefore may improve performance of the heat sink in some application. To facilitation insertion of the heat sink 618' with fins 640' into the inner housing 624b', the inner housing 624b' may define a side opening 664' and a pair of slots 668a-b'. During assembly, the heat sink 618' may be installed in the interior 629' of the inner housing 624b' by fitting the heat sink 618' through the side opening 664' into the slots 668a-b'. The side cover 662' may be installed in side opening 664' to close the inner housing 624b' and entrap the heat sink 618'. The side cover 662' may be secured in place using essentially any desired techniques and apparatus, such as sonic welding or adhesive. As with acoustic module 612, the internal space 629' may be filled with an appropriate phase change material, if desired, to provide improved thermal management.

Figure 31:
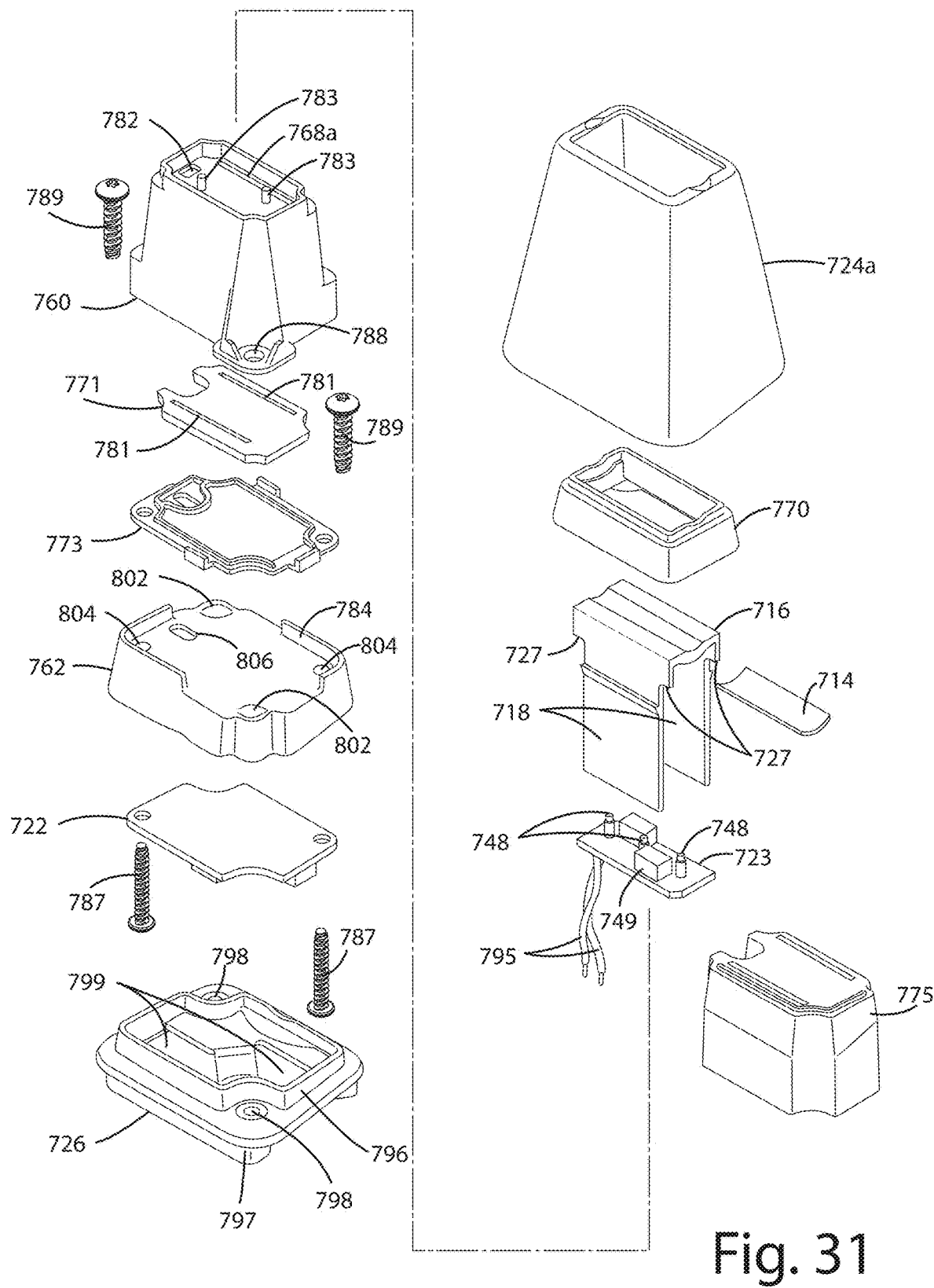
FIG. 31 is an exploded top perspective view of the alternative acoustic module of FIG. 29.
Figure 32:
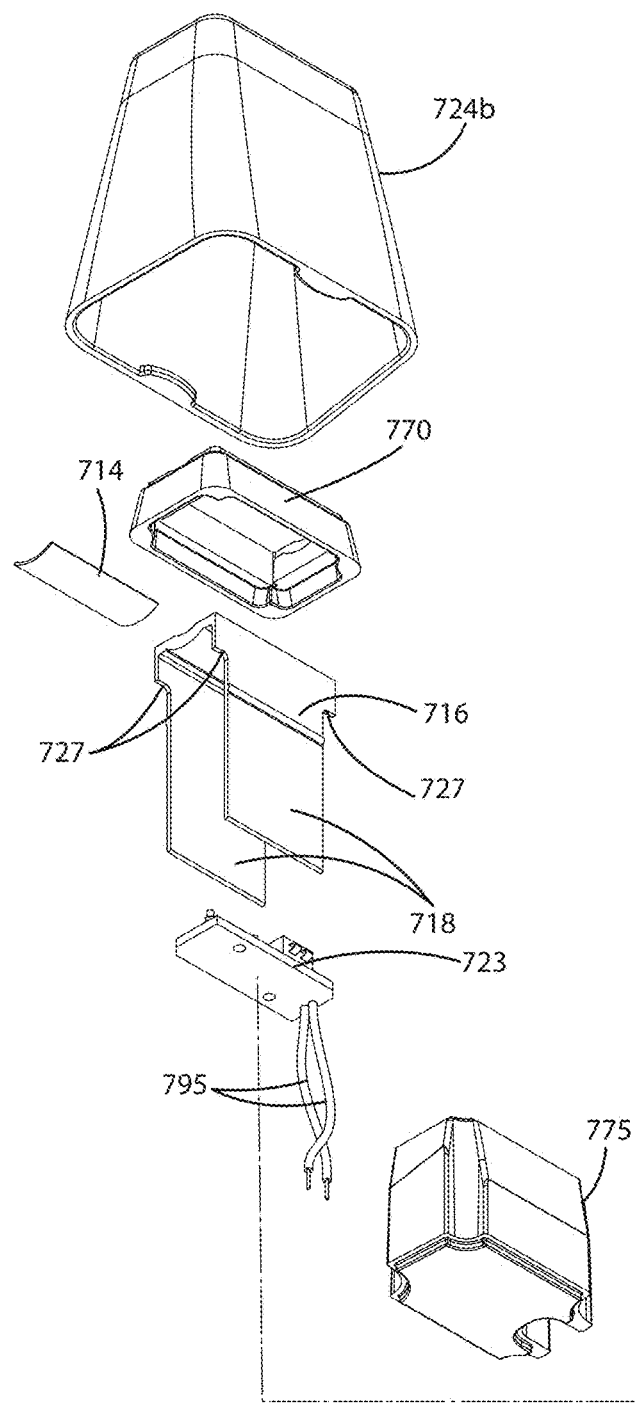
FIG. 32 is an exploded bottom perspective view of the alternative acoustic module of FIG. 29.
Figure 32:
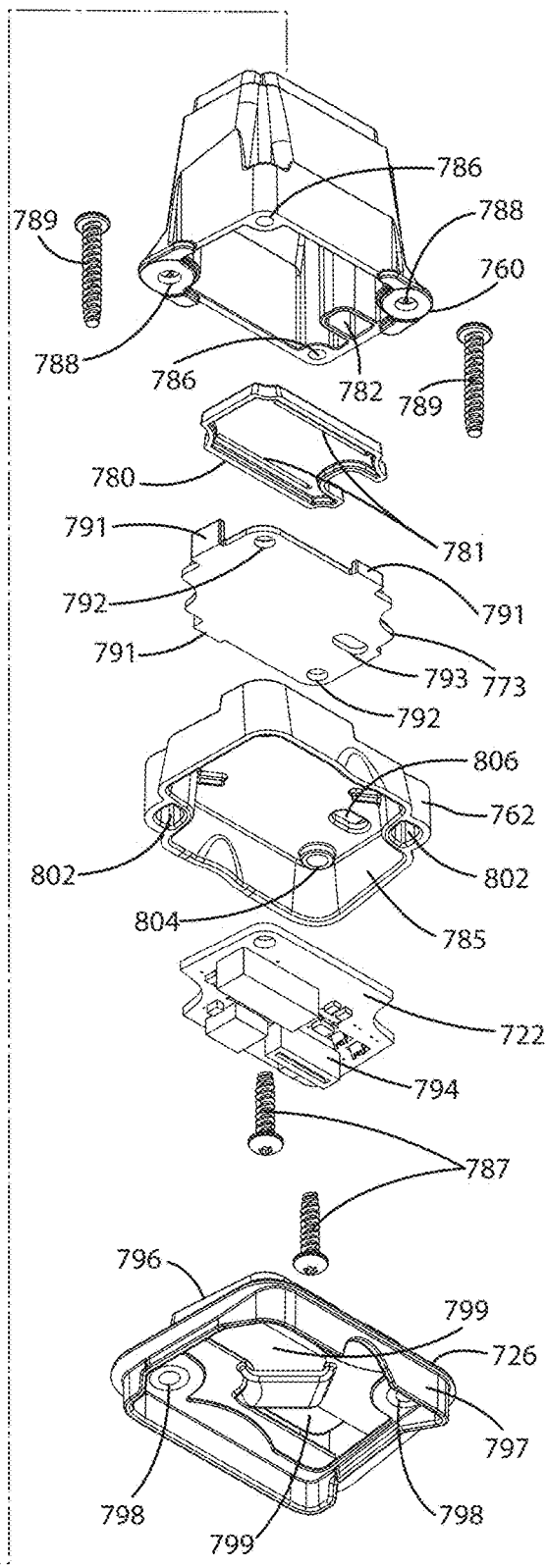

Another alternative acoustic module 712 is shown in FIGS. 29-47. In this embodiment, the acoustic module 712 is generally identical to acoustic module 612, except to the extent described herein and shown in the drawings. Acoustic module 712 will generally be described using reference numerals that correspond with those used in connection with ultrasound device 610, except that the reference numerals will have a "7" in the hundreds digit rather than a "6". For example, the acoustic module will be designated by reference numeral 712 (rather than 612) and the solid waveguide will be designated by reference numeral 716 (rather than 716). Top and bottom exploded perspective views of this alternative embodiment are shown in FIGS. 31 and 32. As shown, this alternative embodiment generally includes an outer housing 724a, a tip gasket 770, a solid waveguide 716 with integral heat sink 718, a transducer 714, a wing gasket 771, a connection PCB 723, an inner housing 724b (including main portion 760 and cover panel 762), a chamber gasket 773, an acoustic module PCB 722 and a cover gasket 726. In this embodiment, the inner housing 724b defines an interior space that may be filled (entirely or partially) with a phase change material 775, such a phase change wax. Alternatively, the interior space may be left empty.

Figures 29, 30:
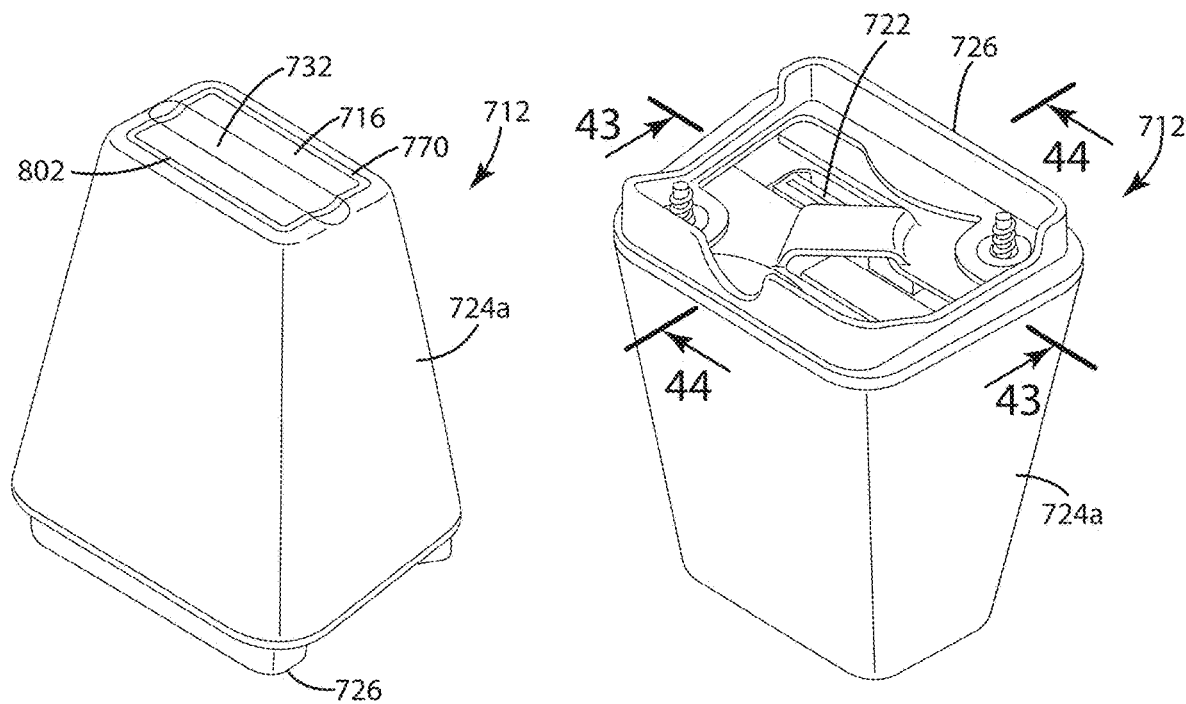
FIG. 29 is a top perspective view of another alternative acoustic module.
FIG. 30 is a bottom perspective view of the alternative acoustic module of FIG. 29.

The solid waveguide 716 of this embodiment generally includes a main body 730 having a target contact surface 732 and a transducer surface 734. In this embodiment, the target contact surface 732 is generally convex following a shallow curved plane that is curved about a single axis. The curvature of the target contact surface 732 is selected to focus acoustic energy along a focal line. As shown in FIG. 29, the target contact surface 732 is generally coextensive with the surface of the outer housing 724a and the surface of tip gasket 770. The transducer surface 734 is disposed on the main body 730 opposite the target contact surface 732. In this embodiment, the transducer surface 734 follows a shallow curved plane that is curved about a single axis. The target contact surface 732 and the transducer surface 734 of the illustrated embodiment are curved about a common axis, which may help to improve focus of acoustic energy along the desired focal line. However, the shape of surfaces may vary and they may have different axes, if desired. The specific geometry of the solid waveguide 716 may vary from application to application. For example, the geometry of the solid waveguide 716 may correspond with the geometry discussed above in connection with solid waveguide 16.

Figure 35:
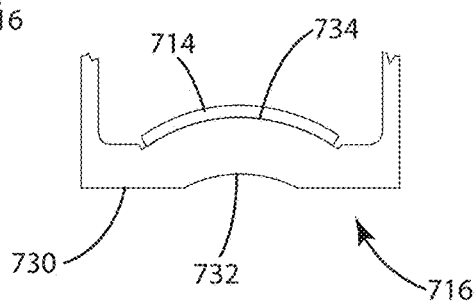
FIG. 35 is an enlarged view of Area A of the solid waveguide of FIG. 34.
Figure 36:
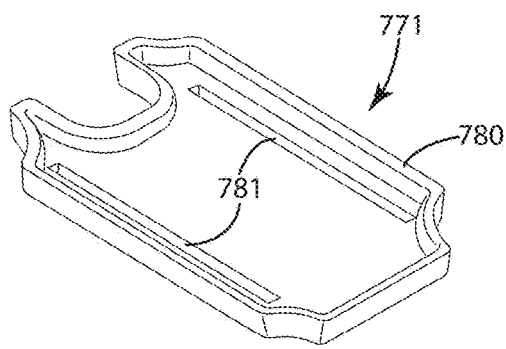
FIG. 36 is a perspective view of the fin gasket.
Figure 37:
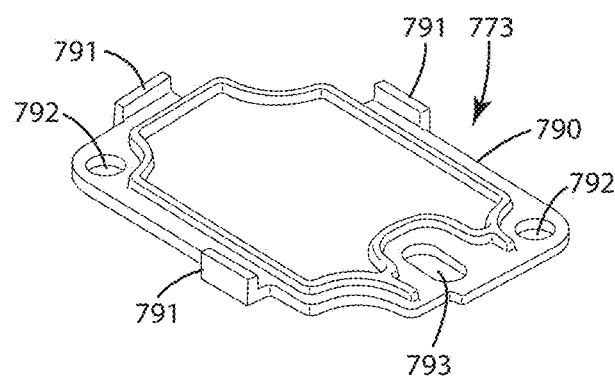
FIG. 37 is a perspective view of the chamber gasket.

The transducer 714 is mounted to the transducer surface 734 of the solid waveguide 716. As shown in FIG. 35, the transducer 714 may be centered on the transducer surface 734 and extend through an arc of about 69.5 degrees. The position and extent of the transducer 714 may, however, vary from application to application. In this embodiment, there is a small gap along opposite longitudinal sides of the transducer 714. The size of the gap may vary, but is approximately 0.01 inches in the illustrated embodiment. The transducer 714 is generally identical to transducer 14 discussed above, and therefore is not discussed in detail here. Suffice it to say that the transducer 714 of this embodiment is a piezo-ceramic component that generates acoustic energy in response to power supplied by the acoustic module PCB 722. It is generally desirable to match the transducer 714 angle to the exiting angle of the target contact surface 732. If the transducer 714 angle exceeds the exiting angle of the target contact surface 732, it could prevent the normal incidence of acoustic waves on the target contact surface 732, and produce multiple internal reflections as well as edge waves, which may compromise overall transducer efficiency.

Figure 43:
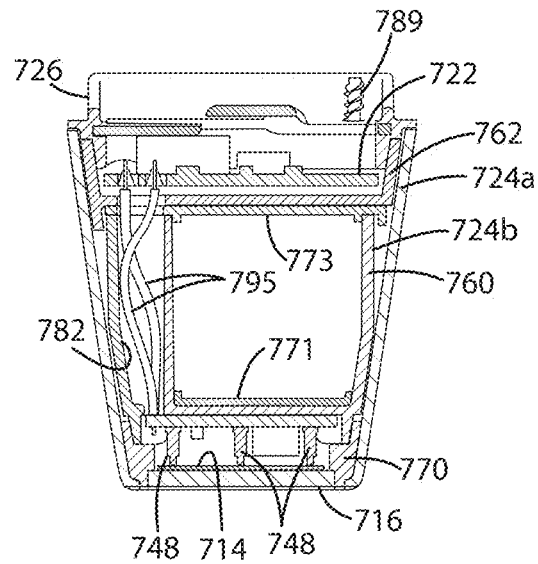
FIG. 43 is a sectional view of the alternative acoustic module of FIG. 29 taken along line 43-43 of FIG. 30.
Figure 44:
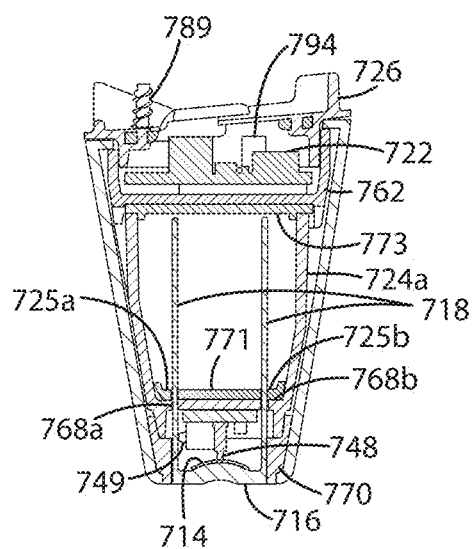
FIG. 44 is a sectional view of the alternative acoustic module of FIG. 29 taken along line 44-44 of FIG. 30.
Figure 45:
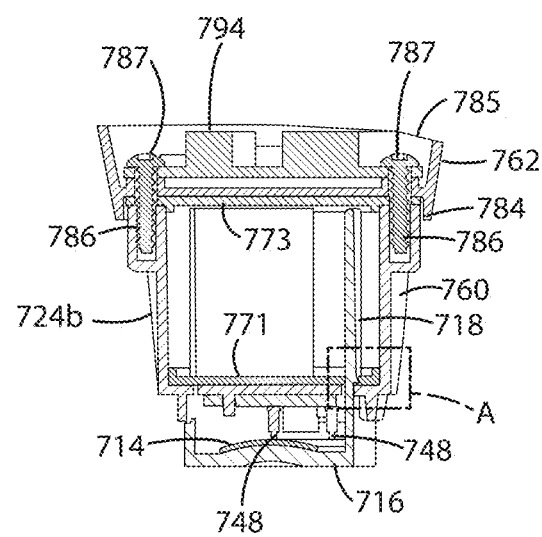
FIG. 45 is a sectional view of the partially assembled alternative acoustic module taken along line 45-45 of FIG. 40.
Figure 46:
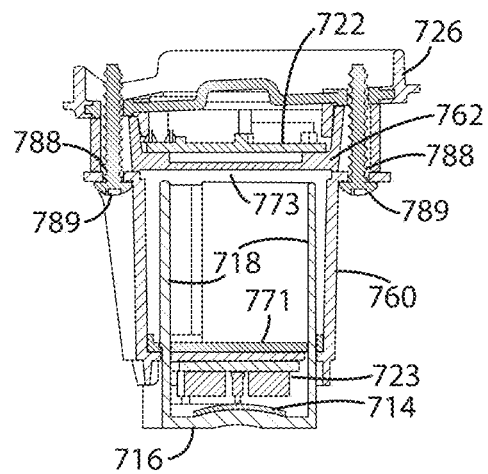
FIG. 46 is a sectional view of the partially assembled alternative acoustic module taken along line 46-46 of FIG. 41.

In this embodiment, the acoustic module 712 includes a connection PCB 723 that provides the connections for electrically coupling the transducer 714 and waveguide 716 to the acoustic module PCB 722. The connection PCB 723 is affixed to the inner housing 724b, for example, by heat stakes 783. The connection PCB 723 may, however, be secured to the inner housing 724b using essentially any suitable connections, such as screws or snaps. The connection PCB 723 may alternatively be secured to the outer housing 724a, the waveguide 716 or the heat sink 718. The connection PCB 723 may include one or more electrical connections for providing electrical contact with the outer exposed surface of the transducer 714. As shown in FIGS. 31 and 43, the connection PCB 723 may include one or more electrical contacts that directly contact the outer exposed surface of the transducer 714. The illustrations show three spring loaded contacts 748, spaced along the length of the transducer 714. The number and location of contacts may vary from application to application. For example, if just one spring-loaded contact is desired, the center location may be populated by the contact. As another example, if two spring-loaded contacts are desired for redundancy, the outer two locations can be populated. Although spring-loaded contacts are shown, other electrical contacts may be used. In this embodiment, the connection PCB 723 also provides an electrical contact with the solid waveguide 714. As perhaps best shown in FIG. 44, the connection PCB 723 may include a right angle, spring-loaded contact 749 that provides a direct electrical connection with a wing of the heatsink 718. Although the spring-loaded contact 749 engages a wing in this embodiment, the contact 749 may alternatively engage essentially anywhere on the solid waveguide 714 or heatsink 718. The number and location of spring-loaded contacts 749 may vary from application to application as desired.

Figure 33:
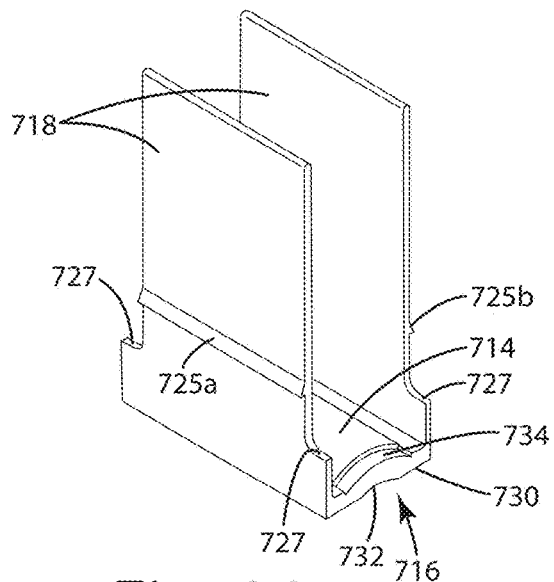
FIG. 33 is a perspective view of the solid waveguide and heat sink of the embodiment of FIG. 29.
Figure 34:
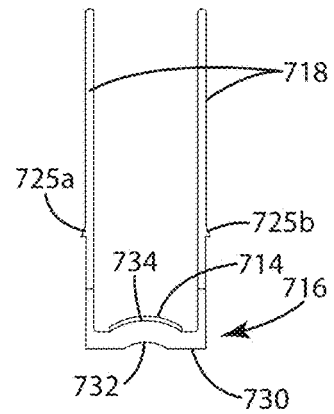
FIG. 34 is a side view of the solid waveguide and heat sink of the embodiment of FIG. 29.
Figure 47:
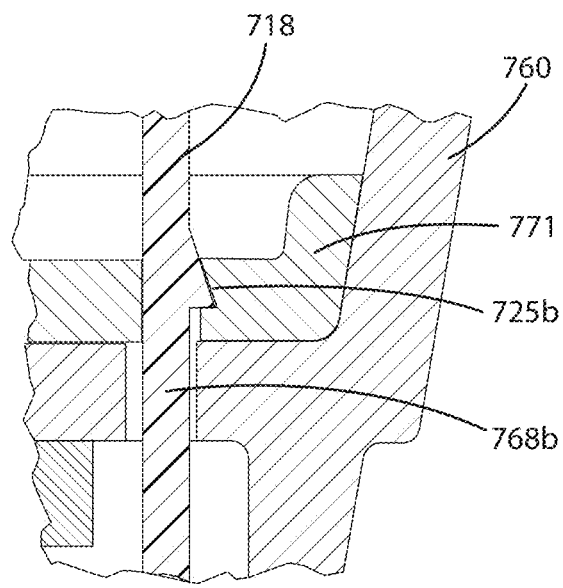
FIG. 47 is an enlarged view of Area A of FIG. 45.

In this embodiment, the solid waveguide 716 includes an integral heat sink 718 that is generally defined by two wings (See FIGS. 33-35). The two wings 718 extend from the solid waveguide 716 into the inner housing 724*b* through slots 768*a*, 768*b*. In this embodiment, each wing of the heat sink 718 includes a barb 725*a-b* that is configured to be snap-fitted into the slots 768*a-b* in the inner housing 724*b*. As shown, the barbs 725*a-b* may be disposed on the outside surfaces of the wings. However, the barbs 725*a-b* may alternatively be positioned on the inside surface of the wings. If desired, barbs may be positioned on the inside and outside surfaces of the wings. In the illustrated embodiment, the barbs 725*a-b* extend essentially the full width of the wings, but that is not necessary. The full-width barbs 725*a-b* may be replaced by one or more short barb segments that extend partially across the width of the wings. The size and shape of the barbs 725*a-b* may be varied to control the amount of force required to install and remove the wings from the inner housing 724*b*. In alternative embodiments, the barbs 725*a-b* may be replaced by other contours or features intended to interfit with the inner housing 724*b*. For example, a semicircular rib may be used in place of a barb 725*a-b* when it is desirable to make it easier to remove the wings from the inner housing 724*b*. In the illustrated embodiment, each wing includes a pair of shoulders 727 that are configured to engage the outer surface of the inner housing 724*b* when the heat sink 718 is properly fitted into the main portion 760. As shown, the shoulders 727 may be defined by a transition in the width of each wing. Referring now to FIG. 47, the barbs 725*a-b* and shoulders 727 cooperatively hold the solid wave guide/heat sink in place with respect to the inner housing 724*b*. In the illustrated embodiment, the spacing between the barbs 725*a-b* and the shoulders 727 is selected to correspond with the thickness of the inner housing 724*b* so the wings snap into place about the inner housing 724*b* with little or no play.

In this embodiment, the inner housing 724*b* includes a main portion 760 and a cover panel 762 that cooperatively define an enclosed interior space that, as noted above, may be fully or partially filled with a phase change material 775 (or left empty). The main portion 760 includes a wire-way 782 that is configured to allow wires to be routed from the acoustic module PCB 722 to the connection PCB 723. In the illustrated embodiment, the wire-way 782 is integrally molded with the main portion 760. Referring to FIG. 43, the wire-way 782 isolates the wires from any phase change material 775 that might be contained in the inner housing 724*b*. The main portion 760 also includes a pair of screw bosses 786 configured to receive screws 787 for securing the acoustic module PCB 722 and cover panel 762 to the main portion 760. As perhaps best shown in FIG. 45, the screws 787 extend through the acoustic module PCB 722, the cover panel 762, the chamber gasket 773, and are received in screw bosses 786. Further, the main portion 720 defines a pair of screw holes 788 configured to receive screws 789 that secure the acoustic module 712 to the ultrasound device. As perhaps best shown in FIG. 46, screws 789 extend through the main portion 760 and the cover gasket 726 and protrude a sufficient distance to engage corresponding screw bosses (not shown) in the ultrasound device. A wing gasket 771 is fitted into the interior of the inner housing 724 to seal the interface between the wings and the main portion 760. As perhaps best shown in FIG. 36, the wing gasket 771 includes a peripheral lip 780 configured to engage the inside surface of the main portion 760 and a pair of slots 781 configured to closely receive the wings. In the illustrated embodiment, the slots 781 and wings interfit tightly enough to create a leaktight seal around the wings to prevent any phase change material from leaking out of the inner housing 724*b* around the wings. In some applications, the barbs 725*a-b* may be configured to bite into the wing gasket 771 to help hold the wing gasket 771 in firm engagement with the main portion 760.

Figure 38:
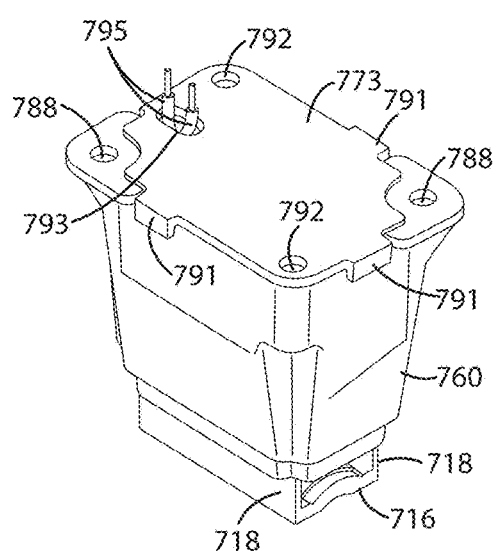
FIG. 38 is a perspective view of the partially assembled acoustic module with the chamber gasket installed.
Figure 39:
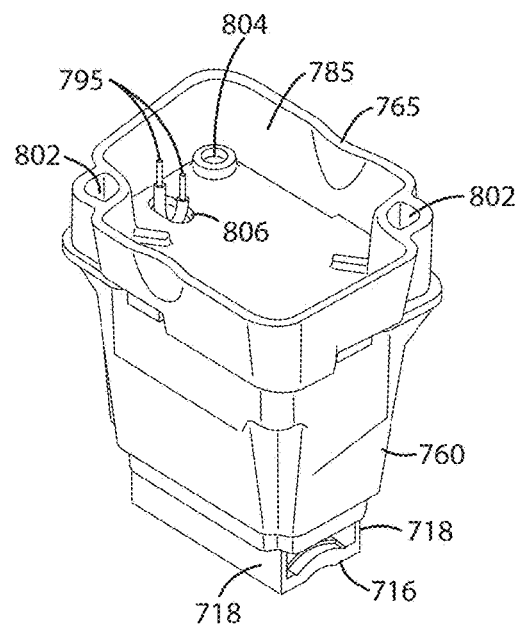
FIG. 39 is a perspective view of the partially assembled acoustic module with the cover installed.

The cover panel 762 is secured to the open end of the main portion 760 to enclose the inner housing 724*b*. FIG. 39 shows the cover panel 762 in position over the open end of the main portion 760. In this embodiment, the cover panel 762 includes an upper peripheral wall 784 that fits closely about the outer perimeter of the main portion 760 and a lower peripheral wall 785 that forms a housing for the acoustic module PCB 722 (See, for example, FIG. 45). The upper peripheral wall 784 may help to reinforce against and resist any expansion of the open top walls of the main portion 760 that might occur as a result of thermal expansion of any PCM material contained in the inner housings 724*b*. The cover panel 762 also defines a pair of screw passages 802 to receive screws 789, a pair of screw holes 804 to receive screws 787 and a wire opening 806 to receive wires 795. A chamber gasket 773 may be disposed between the cover panel 762 in the main portion 762 to provide a leaktight seal. As perhaps best shown in FIG. 37, the chamber gasket 773 generally includes an inner lip 790 that is configured to be closely fitted within the open end of the main portion 760 and a plurality of tabs 791 that are configured to fitted over the outside of the open end of the main portion 760. The inner lip 790 and tabs 791 help to properly locate the chamber gasket 773 with respect to the main portion 760. Also, the tabs 791 may help to hold the chamber gasket 773 in place and prevent it from losing seal if the main portion 760 expands due to thermal expansion of any PCM material that might be contained in the inner housing 724*b*. FIG. 38 shows the chamber gasket 773 positioned over the open end of the main portion. The chamber gasket 773 defines a pair of screw holes 792 configured to provide passage for screws 787 and a wire opening 793 configured to provide passage for the wires 795.

Figure 40:
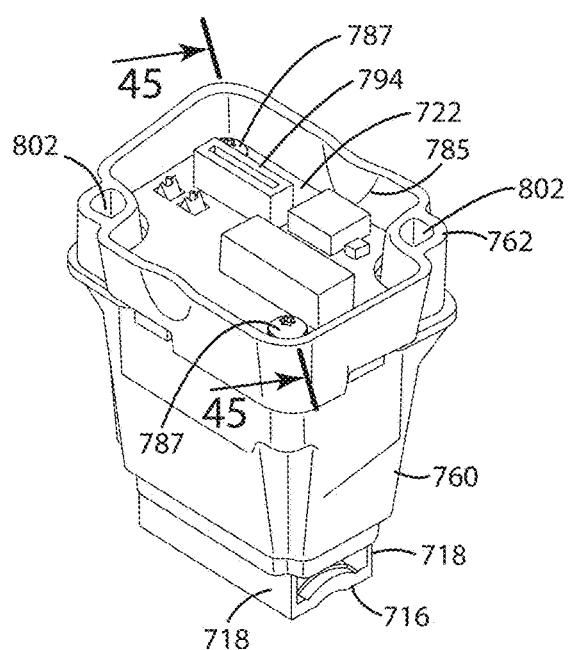
FIG. 40 is a perspective view of the partially assembled acoustic module with the PCB installed.
Figure 41:
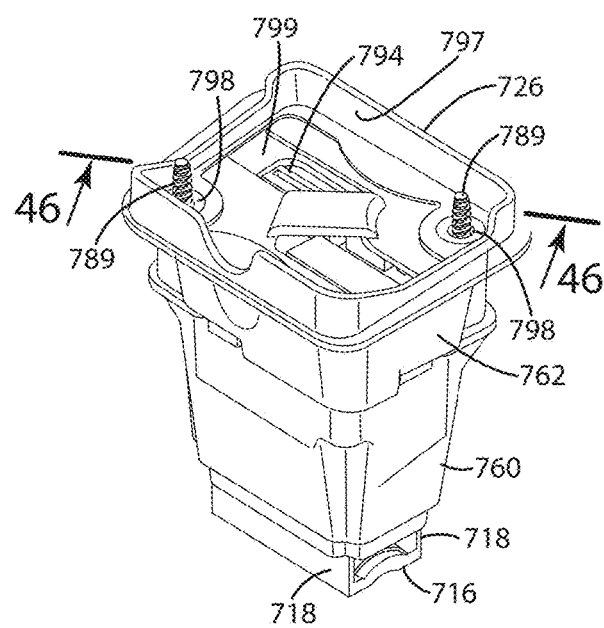
FIG. 41 is a bottom perspective view of the partially assembled acoustic module with the cover gasket installed.

In the illustrated embodiment, the acoustic module PCB 722 is fitted into the cover panel 762 and secured by screws 787 (See FIG. 40). The screws 787 hold the acoustic module PCB 722 and compress the chamber gasket 773 to provide a leaktight seal. The acoustic module PCB 722 is generally identical to acoustic module PCB 22 and therefore will not be described in detail. Suffice it to say that the acoustic module PCB 722 controls operation of the ultrasound device, receiving user input from the user interface and controlling the transducer 714 is accordance with its programming. The acoustic module PCB 722 is operatively coupled to the user interface by a wire ribbon that plugs into port 794 and to the transducer 714 by wires 795 that extend through the wire-way 782 to connection PCB 723. The wire-way 782 isolates the wires 795 from any phase change material 775 that might be present in the interior of the inner housing 724b.

The acoustic module 712 also include a cover gasket 726 that is disposed over the cover panel 762 to provide a leaktight seal between the acoustic module 712 and the handset portion of the ultrasound device. In this embodiment, the cover gasket 726 generally includes an inner lip 796 configured to be fitted closely into the cover panel 760 and an outer lip 797 configured to be closely fitted into the handset portion of the ultrasound device. The cover gasket 726 of this embodiment defines a pair of screw holes 798 to allow passage of screws 789 and at least one central opening 799 to allow routing of the wire ribbon (not shown) from the user interface to the acoustic module PCB 722.

Figure 42:
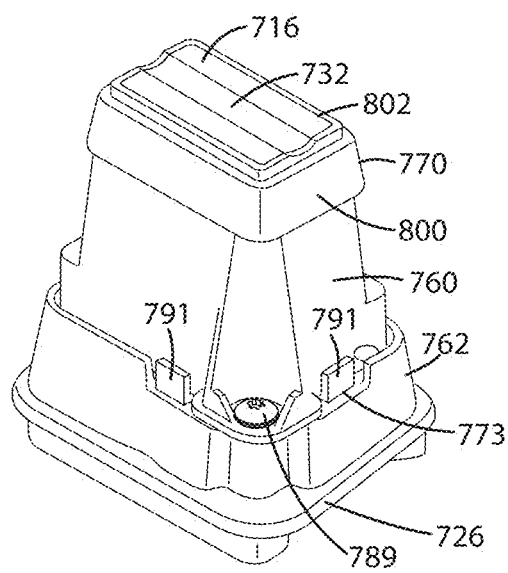
FIG. 42 is a top perspective view of the partially assembled acoustic module with the tip gasket installed.

As noted above, the acoustic module 712 also includes a tip gasket 770. FIG. 42 shows the tip gasket 770 fitted over the partially assembled acoustic module 712. As perhaps best shown in FIGS. 43 and 44, the tip gasket 770 occupies the space between the main portion 760, the solid waveguide 716 and the outer housing 724a. In this embodiment, the tip gasket 770 includes a peripheral member 800 that is configured to be closely fitted about the end of the main portion 760 and the periphery of the solid waveguide 714. The tip gasket 770 also includes a lip 802 that extends through a narrow gap between the solid waveguide 716 and the outer housing 724a and forms a portion of the outer surface of the acoustic module 712. In this embodiment, the lip 802 is generally coextensive with the target contact surface of the solid waveguide 716 and the adjacent portions of the outer housing 724a.

The tip gasket 770, wing gasket 771, chamber gasket 773 and cover gasket 726 may be manufactured from essentially any material suitable for use in forming a leaktight seal, such as rubber, nitrile rubber, silicone, PTFE or a plastic polymer. For example, the various gaskets may be molded using conventional techniques and apparatus.

Control System.

It is desirable to provide an acoustic module that provides uniform acoustic energy transmission along the longitudinal length of the solid waveguide. The greater the uniformity in energy transmission, the greater the uniformity in delivered thermal field across the full longitudinal length of the acoustic device. This uniform distribution of energy lends itself to a better consumer experience with no asymmetric concentration of energy which can lead to hotspots. The field uniformity ratio is a metric used to describe this aspect of ultrasound and is based on peak-to-trough intensity differences along a plane at the focus of the acoustic module. The field uniformity is generally frequency dependent as the wave interferences and wave numbers change with frequency at the focal point of the device. For the solid waveguide, this can be even more accentuated with the concavity of the solid waveguide giving rise to different wave number effects as frequencies change. Differences in epoxy (or other adhesive) thickness, impurity location in aluminum material matrix and other dimensional tolerance issues along the delay path, only make this variation more unpredictable between acoustic modules in a functional setting.

The present invention also provides a control methodology that provides improved uniformity in the acoustic field in the longitudinal direction. Generally, the present invention implements a method of using a frequency sweep during the application of operating power across a predefined uniformity scan window on either side of the operating resonant frequency, to help smooth the acoustic uniformity curve (See FIGS. 19-21B). Additionally, the predefined uniformity scan window can be adjusted dynamically to compensate for acoustic transducer efficiency loss, as a tradeoff exists between uniformity sweep frequency range and transducer efficiency loss. Moreover, the electrical driving voltage can also be adjusted dynamically at each frequency sweep step to achieve a more consistent acoustic power output. In practice, variations along the longitudinal length of the transducer and delay path give the acoustic module different peak operating frequencies at different points along the longitudinal length of the acoustic module. Operating at a single operating frequency produces greater intensity at those points with a corresponding peak operating frequency and lesser intensity at those points with a different peak operating frequency. By sweeping through a range of frequencies that includes the different peak operating frequencies while applying operating power, the system can dramatically improve overall acoustic uniformity. For example, FIG. 20A is a thermal image and FIG. 20B is a line graph at focus of an acoustic module that does not use a uniformity scan algorithm in accordance with the present invention. As can be seen, the thermal output varies significantly along the longitudinal length of the acoustic module. FIG. 21A is a thermal image and FIG. 21B is a line graph at focus of the same acoustic module implementing a uniformity scan algorithm. It can be seen by comparison of FIGS. 20A-B with FIGS. 21A-B that the overall uniformity is significantly improved by the uniformity scan method, with the hottest areas in FIG. 20A being reduced in temperature and the coolest areas in FIG. 20A being increased in temperature.

In practice, the controller implements the uniformity scan over a frequency range (e.g. uniformity scan window size) with an appropriate frequency step size. In some applications, the uniformity scan window size and step size are determined in advance. For example, in some applications, it may be desirable to determine the uniformity scan window size and step size on a product-by-product basis. More specifically, it may be desirable to test each acoustic module after production to assess its inherent acoustic properties to determine the appropriate uniformity scan window size for that acoustic module. In applications in which acoustic modules are manufactured with sufficient consistency, the uniformity scan parameters may be determined for all products of a particular design rather than on a product-by-product basis. As described below, the uniformity scan parameters may be determined, in part, based on an efficiency sweep over a frequency range associated with the acoustic module's operating frequency. In this application, the operating point (i.e. point of maximum efficiency) of each acoustic module is determined after manufacture using convention tuning procedures. For example, operating power may be applied to the acoustic module at various operating frequencies to determine which operating frequency provides maximum efficiency. Generally speaking, the operating point of each acoustic module will be in the range of 5 MHz+/−0.5 MHz or 4 to 5.5 MHz, but this operating point may vary from application to application depending on the design and configuration of the transducer and/or the waveguide.

Figure 19:
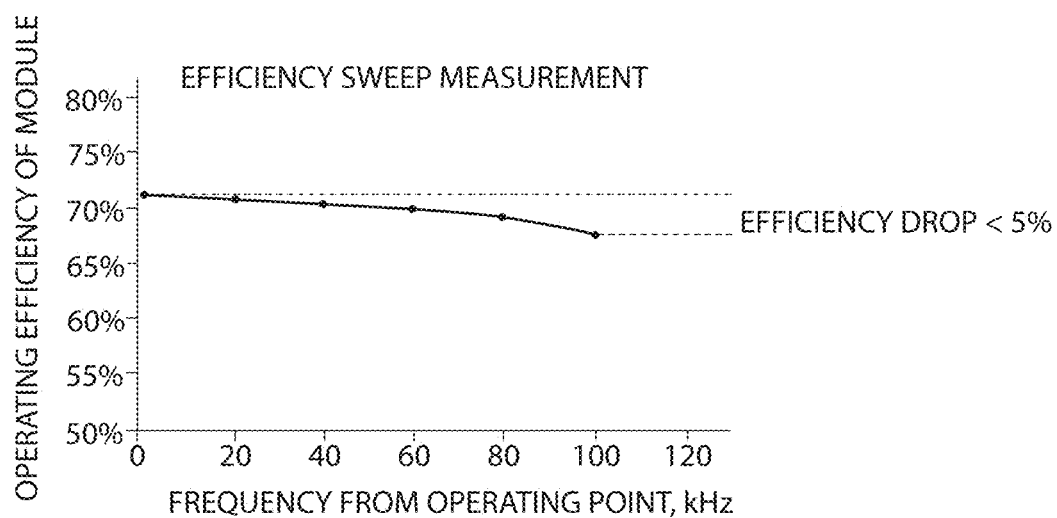
FIG. 19 is a graph showing a plot of acoustic module efficiency against frequency.
Figure 22:
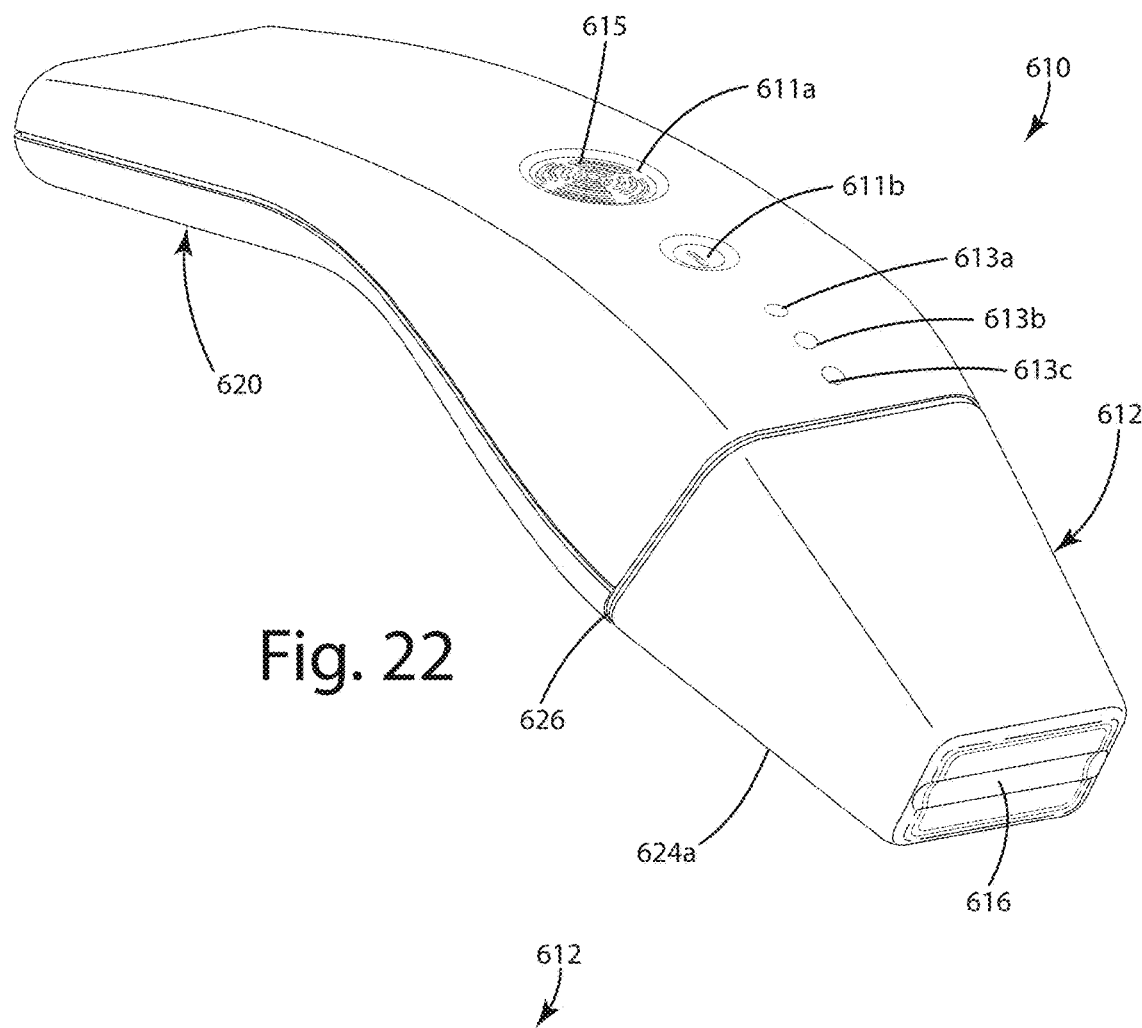
FIG. 22 is a perspective view of an alternative ultrasound device.

An implementation of the method for determining uniformity scan parameters will now be described with reference to FIG. 19. FIG. 19 shows the efficiency sweep results from a frequency sweep performed on the positive side of the operating point. In this embodiment, it is assumed that efficiency will be sufficiently symmetrical about the operating point that it is unnecessary to perform a frequency sweep on both the positive and negative sides of the operating point. Instead, it is assumed that the negative side will largely mirror the positive side efficiency sweep results and the uniformity scan window is determined based solely on the positive side efficiency measurements. Alternatively, the efficiency sweep can be performed on only the negative side or through both the negative and positive sides of the operating point. In the illustrated embodiment, a frequency sweep efficiency measurement is taken on the positive side of the module's operating frequency in 20 KHz steps. Although this efficiency sweep is performed in 20 KHz steps, the step size can vary from application to application as desired. In this embodiment, the range of this efficiency sweep is dictated by the maximum frequency window allowable by electronics during treatment, but the range may be dictated by other factors. For example, the efficiency sweep range may be selected based on maximum and minimum values obtained through experience. After the efficiency sweep has been performed, the uniformity scan window size is selected to be the largest possible uniformity window sweep size that results in the maximum acceptable efficiency loss, which in this embodiment is 5% or less. In this case, the uniformity scan window size is selected to be 200 KHz (i.e. from 100 KHz below the operating point to 100 KHz above the operating point). The maximum efficiency drop may vary from application to application, as desired. For example, in applications where efficiency is of greater importance, the maximum efficiency drop may be lowered to essentially any value between 5% and 0%. As another example, in applications where efficiency is of lesser importance, the maximum efficiency drop may be increased to a value greater than 5%.

In operation, the controller may be configured to apply operating power to the transducer over fixed operating time periods. The operating time period may be set based on acoustic energy output rates and the corresponding impact on the target. The illustrated embodiment is intended for use as a therapeutic device that applies acoustic energy to human skin, such as to portions of the face to reduce fine lines and wrinkles. In this context, the controller of the illustrated embodiment applies power to the transducer in fixed operating time increments of seven seconds, but the fixed operating time may vary from application to application. In some applications, the operating time may not be fixed. During each period of operation, the controller is configured to continuously and repeatedly sweep through the determined frequency scan window at a determined step size and step time. A single sweep may include sweeping through the frequency scan window from the minimum frequency to the maximum frequency and then back to the minimum frequency, or it may include sweeping between the maximum and minimum frequencies in only one direction (i.e. from minimum to maximum or from maximum to minimum) or it may include a random sweep. Step size and step time may be determined based on a wide variety of alternative methods. For purposes of disclosure, one suitable method for determining step size and step time will be described. In this embodiment, the step size and step time are determined after the appropriate frequency scan window has been determined. In the illustrated embodiment, the uniformity frequency scan step size is 20 KHz. Experimentation has demonstrated that this is an appropriate step size for the intended application of the illustrated embodiment. The step size may, however, vary from application to application, as desired. For example, a larger or smaller step size may be implemented when doing so would provide improved uniformity and/or improved efficiency, or when dictated by practical limitations presented by the related electronics. To determine the number of steps in the uniformity scan sweep, the size of each step (e.g. 20 KHz in this embodiment) is divided into the total width of the frequency scan window (e.g. 200 KHz in this embodiment). The number of steps is then divided into the overall time of the uniformity frequency scan sweep to determine the amount of time that the controller is to remain at each step during the scan. In this embodiment, the length of time of each sweep is about $1/500^{th}$ or about $1/1000^{th}$ of a second, which were determined to be appropriate for the intended application through experimentation. The length of time of each uniformity frequency scan sweep may vary from application to application. In some applications, a more rapid sweep or a slower sweep may provide improved performance (e.g. efficiency, uniformity or other parameters). Generally speaking, the frequency of the uniformity scan sweep will often, but not necessarily, be (a) between about 10 to about 1,000 sweeps per second of operating time or (b) between about 200 to 500 sweeps per second of operating time or (c) about 500 sweeps per second of operating time. It should be understood that this method for determining step size and step time is merely exemplary. The step size and step time may vary from application to application, as desired. For example, the described method provides substantially linear movement through the frequency scan window. A nonlinear method may be implemented when nonlinear movement might provide improved efficiency, improved uniformity or provide other practical benefits. For example, a mathematical analysis of the efficiencies of the acoustic module at each step in the frequency scan may be used to provide an optimized sweep profile that provides optimized efficiency and optimized uniformity.

Following determination, the uniformity scan sweep parameters may be programmed into the controller for use during operation of the acoustic module. The controller may be configured to implement the uniformity frequency scan while supplying operating power to the transducer. More specifically, the controller may be programmed to continuously and repeatedly sweep through the uniformity scan sweep window at all times while supplying operating power to the transducer. In this embodiment, the controller is programmed to vary the frequency of the electrical signal applied to the transducer in accordance with the uniformity scan sweep parameters so that the transducer provides improved uniformity while maintaining the desired efficiency. In some applications, it may be desirable not to implement the uniformity frequency sweep continuously during the supply of operating power.

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

The invention claimed is:

1. An acoustic module comprising:
a one-piece solid waveguide, said waveguide having a first surface with a first curvature and a second surface with a second curvature, said second surface configured to contact a target, said first and second curvatures selected to focus acoustic energy along a focal line a predetermined distance from said second surface into a target;
an ultrasound transducer disposed on said first surface, said ultrasound transducer having a curvature corresponding with said first curvature; and
a controller operably coupled to said ultrasound transducer, said controller configured to direct supply of power to said ultrasound transducer at a plurality of operating frequencies, said controller configured to obtain a measured characteristic at each of a first plurality of operating frequencies at which power is supplied to said ultrasound transducer, said controller configured to determine a second plurality of operating frequencies for operation based on 1) the plurality of measured characteristics obtained with respect to said first plurality of operating frequencies and 2) said second plurality of operating frequencies providing an efficiency loss less than a threshold efficiency loss, said controller configured to supply power to said ultrasound transducer according to said second plurality of operating frequencies to provide acoustic energy to the target with said efficiency loss being less than said threshold efficiency loss.

2. The acoustic module of claim 1 wherein said first curvature and said second curvature are curved about a common axis.

3. The acoustic module of claim 2 wherein said transducer includes a first conductive plate and a second conductive plate, said second conductive plate being electrically connected to said waveguide.

4. The acoustic module of claim 3 further including a first electrode and a second electrode for applying an electrical signal to said transducer, said first electrode being electrically connected to said first conductive plate, said second electrode being electrically connected to said waveguide; and
further including an electrically conductive adhesive disposed between said transducer and said waveguide, whereby said second electrode is electrically connected to said second conductive plate.

5. The acoustic module of claim 1 wherein said waveguide includes an integral skirt extending in a direction opposite said second surface to provide a thermal mass.

6. The acoustic module of claim 1 wherein said waveguide defines a first longitudinal slot extend along one longitudinal side of said waveguide and a second longitudinal slot extend along an opposite longitudinal side of said waveguide, said slots approaching but not extending into an acoustic flow path between said first surface and said second surface.

7. The acoustic module of claim 6 further including a heat sink fitted into at least one of said slots.

8. The acoustic module of claim 6 further including a first heat sink fitted into said first longitudinal slot and a second heat sink fitted to said second longitudinal slot.

9. The acoustic module of claim 1 wherein said acoustic module defines an enclosed space rearward of said transducer in a direction opposite of said second surface; and
further including a phase change material disposed in said enclosed space.

10. The acoustic module of claim 9 wherein said phase change material is a paraffin wax.

11. The acoustic module of claim 9 wherein said phase change material is a microencapsulated phase change powder.

12. The acoustic module of claim 1 wherein said acoustic module includes an active ventilation system having an enclosure with an inlet, an outlet and a fan drawing air into said enclosure through said inlet and discharging air from said enclosure through said outlet.

13. The acoustic module of claim 12 wherein said inlet and said outlet are covered by a ventilation material.

14. The acoustic module of claim 1 wherein said waveguide includes an epoxy frame closely surrounding a periphery of said transducer.

15. The acoustic module of claim 1 wherein said first surface defines a transducer recess, said transducer recess closely receiving said transducer along at least two sides to facilitate alignment between said transducer and said waveguide.

16. The acoustic module of claim 15 wherein said transducer recess includes an extension portion.

17. The acoustic module of claim 1 wherein said waveguide is a one-piece extrusion.

18. The acoustic module of claim 1 wherein said waveguide includes an integral heat sink, said waveguide and said integral heat sink being a one-piece extrusion.

19. The acoustic module of claim 1 wherein said second surface is coated.

20. The acoustic module of claim 1 wherein said controller is operable to direct repeated sweeping of said second plurality of operating frequencies.

21. The acoustic module of claim 1 wherein said measured characteristic is indicative of an efficiency of operation of the acoustic module at each of said first plurality of operating frequencies.

22. The acoustic module of claim 1 comprising at least one spring-loaded contact operable to form an electrical connection with said ultrasound transducer, wherein power is supplied to said ultrasound transducer via said at least one spring-loaded contact.

23. An acoustic module comprising:
an inner housing defining an internal space;
a solid waveguide having a transducer surface and a target contact surface, said target contact surface having a first curvature selected to focus acoustic energy along a focal line a predetermined distance from said target contact surface into a target, said waveguide disposed outside of said internal space;
a heat sink extending from said waveguide, said heat sink including at least one wing extending from said waveguide into said internal space;

a transducer disposed on said transducer surface, said transducer having a curvature corresponding with said first curvature;

a controller operably coupled to said transducer, said controller configured to direct supply of power to said transducer at a plurality of operating frequencies, said controller configured to obtain a measured characteristic at each of a first plurality of operating frequencies, said controller operable to determine a second plurality of operating frequencies for said transducer based on 1) said plurality of measured characteristics obtained with respect to said first plurality of operating frequencies and 2) said second plurality of operating frequencies providing an efficiency loss less than a threshold efficiency loss, said controller configured to supply power to said transducer according to said second plurality of operating frequencies to provide acoustic energy to the target with said efficiency loss being less than said threshold efficiency loss; and an outer housing disposed about said inner housing, said waveguide, said heat sink and said transducer, said outer housing defining an opening, said target contact surface exposed by said opening.

24. The acoustic module of claim 23 including a phase change material disposed in said internal space.

25. The acoustic module of claim 24 wherein said phase change material is a phase change wax.

26. The acoustic module of claim 24 further including a wing gasket disposed about a perimeter of said internal space and about said at least one wing.

27. The acoustic module of claim 26 wherein said inner housing includes a first portion and a second portion; and
further including a chamber gasket disposed between said first portion and said second portion.

28. The acoustic module of claim 24 further including an acoustic module PCB and a connection PCB, said connection PCB electrically connected to said acoustic module PCB by electrical conductors; and
wherein said inner housing includes a wire-way, said electrical conductors extending from said acoustic module PCB to said connection PCB through said wire-way, said wire-way configured to isolate said electrical conductors from said phase change material in said internal space.

29. The acoustic module of claim 23 wherein said inner housing defines at least one slot, said at least one wing extending through said slot, said at least one wing including a protrusion interfitted with said inner housing to mechanically secure said wing within said inner housing.

30. The acoustic module of claim 29 wherein said protrusion includes a barb.

31. The acoustic module of claim 23 wherein said heat sink includes two wings; and
wherein said inner housing defines two slots, each of said wings extending through a different one of said slots, each of said wings including a protrusion interfitted with said inner housing to mechanically secure said wings within said inner housing.

32. The acoustic module of claim 23 further including an acoustic module PCB and a connection PCB, said connection PCB electrically connected to said acoustic module PCB and affixed to said inner housing, said connection PCB including a first electrical contact engaging said transducer and a second electrical contact engaging at least one of said waveguide and said heat sink.

33. The acoustic module of claim 32 wherein said first electrical contact is a spring-loaded contact.

34. The acoustic module of claim 33 wherein said second electrical contact is a spring-loaded contact.

35. The acoustic module of claim 23 wherein said waveguide is a one-piece extrusion.

36. The acoustic module of claim 23 wherein said waveguide and said heat sink are integral and are a one-piece extrusion.

37. The acoustic module of claim 23 wherein said target contact surface is coated.

38. The acoustic module of claim 23 wherein said controller is operable to direct repeated sweeping of said second plurality of operating frequencies in order to direct acoustic energy into the target.

39. The acoustic module of claim 23 wherein said measured characteristic is indicative of an efficiency of operation of the acoustic module at each of said first plurality of operating frequencies.

40. The acoustic module of claim 23 comprising at least one spring-loaded contact operable to form an electrical connection with said transducer, wherein power is supplied to said transducer via said at least one spring-loaded contact.

41. An acoustic module comprising:
a waveguide configured to direct acoustic energy into a target;
an ultrasound transducer disposed on a first surface of the said waveguide; and
a controller operably coupled to said ultrasound transducer, said controller configured to direct supply of power to said ultrasound transducer by directing a frequency sweep at a plurality of frequencies, said controller configured to obtain a plurality of measurements with respect to said frequency sweep, said controller configured to determine a plurality of operating frequencies for supplying power to said ultrasound transducer based on said plurality of measurements and said plurality of operating frequencies providing an efficiency loss less than a threshold efficiency loss.

42. The acoustic module of claim 41 wherein said controller is configured to obtain one or more measured characteristics respectively at one or more frequencies of operation, said controller configured to determine said plurality of operating frequencies based on said one or more measured characteristics.

43. The acoustic module of claim 42 wherein said one or more measured characteristics are indicative of an efficiency of operation of the acoustic module respectively at said one or more frequencies of operation.

44. The acoustic module of claim 41 wherein:
said first surface of said waveguide includes a first curvature;
said waveguide includes a second surface with a second curvature;
second surface is configured to contact a target;
said first and second curvatures are selected to focus acoustic energy along a focal line a predetermined distance from said second surface into a target; and
said ultrasound transducer includes a curvature corresponding to said first curvature.

45. The acoustic module of claim 41 wherein said waveguide is a one-piece solid waveguide.

46. The acoustic module of claim 41 comprising at least one spring-loaded contact operable to form an electrical connection with said ultrasound transducer, wherein power is supplied to said ultrasound transducer via said at least one spring-loaded contact.

* * * * *

UNITED STATES PATENT AND TRADEMARK OFFICE
CERTIFICATE OF CORRECTION

| | |
|---|---|
| PATENT NO. | : 11,241,591 B2 |
| APPLICATION NO. | : 15/234217 |
| DATED | : February 8, 2022 |
| INVENTOR(S) | : Ronald L. Stoddard et al. |

It is certified that error appears in the above-identified patent and that said Letters Patent is hereby corrected as shown below:

In the Claims

Column 30, Claim 41, Lines 26-27:
"an ultrasound transducer disposed on a first surface of the said waveguide; and"
Should be:
--an ultrasound transducer disposed on a first surface of said waveguide; and--

Signed and Sealed this
Thirty-first Day of May, 2022

Katherine Kelly Vidal
*Director of the United States Patent and Trademark Office*